(12) United States Patent
Tatsuta et al.

(10) Patent No.: US 8,618,170 B2
(45) Date of Patent: Dec. 31, 2013

(54) ORAL FORMULATIONS OF BIS(THIOHYDRAZIDE AMIDES)

(75) Inventors: Noriaki Tatsuta, Lexington, MA (US); Takayo Inoue, Malden, MA (US); Keizo Koya, Chestnut Hill, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 405 days.

(21) Appl. No.: 12/741,486

(22) PCT Filed: Nov. 7, 2008

(86) PCT No.: PCT/US2008/012613
§ 371 (c)(1),
(2), (4) Date: Aug. 17, 2010

(87) PCT Pub. No.: WO2009/064374
PCT Pub. Date: May 22, 2009

(65) Prior Publication Data
US 2010/0311840 A1    Dec. 9, 2010

Related U.S. Application Data

(60) Provisional application No. 61/002,623, filed on Nov. 9, 2007.

(51) Int. Cl.
*A61K 31/16* (2006.01)

(52) U.S. Cl.
USPC .......................................... 514/614; 514/615

(58) Field of Classification Search
None
See application file for complete search history.

(56) References Cited

U.S. PATENT DOCUMENTS

| | | | | |
|---|---|---|---|---|
| 6,538,020 B2 * | 3/2003 | Joshi-Hangal et al. | ........ | 514/449 |
| 6,762,204 B2 * | 7/2004 | Koya et al. | ........ | 514/599 |
| 6,800,660 B2 * | 10/2004 | Koya et al. | ........ | 514/614 |
| 6,825,235 B2 | 11/2004 | Chen et al. | | |
| 6,924,312 B2 * | 8/2005 | Koya et al. | ........ | 514/614 |
| 7,001,923 B2 * | 2/2006 | Koya et al. | ........ | 514/599 |
| 7,037,940 B2 * | 5/2006 | Koya et al. | ........ | 514/599 |
| 7,074,952 B2 | 7/2006 | Chen et al. | | |
| 7,345,094 B2 * | 3/2008 | Koya et al. | ........ | 514/599 |
| 7,368,473 B2 * | 5/2008 | Koya et al. | ........ | 514/449 |
| 7,385,084 B2 * | 6/2008 | Koya et al. | ........ | 564/74 |
| 7,435,843 B2 | 10/2008 | Chen et al. | | |
| 7,579,503 B2 * | 8/2009 | Koya et al. | ........ | 564/74 |
| 7,645,904 B2 | 1/2010 | Chen et al. | | |
| 7,652,168 B2 | 1/2010 | Chen et al. | | |
| 7,671,092 B2 * | 3/2010 | Koya et al. | ........ | 514/599 |
| 7,678,832 B2 | 3/2010 | Lunsmann et al. | | |
| 7,709,683 B2 | 5/2010 | Chen et al. | | |
| 7,750,042 B2 * | 7/2010 | Koya et al. | ........ | 514/449 |
| 7,763,658 B2 * | 7/2010 | Koya et al. | ........ | 514/599 |
| 7,795,313 B2 * | 9/2010 | Koya et al. | ........ | 514/599 |
| 7,939,564 B2 * | 5/2011 | Koya | ............... | 514/599 |
| 8,048,925 B2 * | 11/2011 | Koya et al. | ........ | 514/599 |
| 8,093,425 B2 * | 1/2012 | Koya et al. | ........ | 564/149 |
| 2006/0142386 A1 | 6/2006 | Barsoum et al. | | |
| 2006/0142393 A1 | 6/2006 | Sherman et al. | | |
| 2006/0167106 A1 | 7/2006 | Zhang et al. | | |
| 2007/0088057 A1 | 4/2007 | Lunsmann et al. | | |
| 2008/0118562 A1 | 5/2008 | Koya et al. | | |
| 2008/0176828 A1 | 7/2008 | Williams et al. | | |
| 2008/0226588 A1 | 9/2008 | McLeod et al. | | |
| 2009/0023736 A1 | 1/2009 | Koya et al. | | |
| 2009/0042991 A1 | 2/2009 | Barsoum et al. | | |
| 2009/0093538 A1 | 4/2009 | Bertin et al. | | |
| 2009/0137682 A1 | 5/2009 | Dahl et al. | | |
| 2010/0068174 A1 | 3/2010 | Jacobson et al. | | |
| 2010/0081635 A1 | 4/2010 | Chen et al. | | |
| 2010/0093828 A1 | 4/2010 | Koya et al. | | |
| 2010/0249239 A1 | 9/2010 | Lunsmann et al. | | |
| 2010/0280075 A1 | 11/2010 | Koya et al. | | |
| 2010/0324143 A1 | 12/2010 | Koya et al. | | |
| 2011/0098476 A1 | 4/2011 | Chen et al. | | |

FOREIGN PATENT DOCUMENTS

| | | |
|---|---|---|
| JP | 52-15549 | 2/1977 |
| WO | WO 2006/113493 | 10/2006 |
| WO | WO 2008/024301 | 2/2008 |
| WO | WO 2008/024302 | 2/2008 |
| WO | WO 2008/024305 | 2/2008 |
| WO | WO 2008/027445 | 3/2008 |

(Continued)

OTHER PUBLICATIONS

National Institute for Health and Clinical Excellence, Health Technology Appraisal, Docetaxel and paclitaxel as adjuvant therapy in early breast cancer, Scope, Sep. 2005, available at http://www.nice.org.uk/nicemedia/pdf/BreastCancerearlyDocetaxelandpaclitaxel_finalscope.pdf.*

(Continued)

*Primary Examiner* — Sreeni Padmanabhan
*Assistant Examiner* — Svetlana M Ivanova
(74) *Attorney, Agent, or Firm* — McCarter & English, LLP; Steven G. Davis

(57) ABSTRACT

Disclosed herein are oral formulations of bis(thio-hydrazide amides) compounds of the following structural formula (I): or a pharmaceutically acceptable salt thereof, wherein $R_1$, $R_2$, $R_3$, $R_4$, $R_7$, $R_8$, Z, and Y are defined herein.

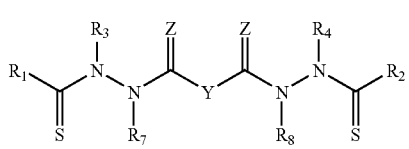

25 Claims, 1 Drawing Sheet

(56) References Cited

FOREIGN PATENT DOCUMENTS

| WO | WO 2009/020631 | 2/2009 |
| --- | --- | --- |
| WO | WO 2009/064374 | 5/2009 |
| WO | WO 2009/073147 | 6/2009 |
| WO | WO 2009/073148 | 6/2009 |
| WO | WO 2010/048284 | 4/2010 |
| WO | WO 2010/048293 | 4/2010 |
| WO | WO 2010/065512 | 6/2010 |
| WO | WO 2011/069159 | 6/2011 |

OTHER PUBLICATIONS

Furuse et al., J. Clin. Oncology, vol. 17, No. 9 (Sep.): pp. 2692-2699.*

Expert Panel Statement, Determination of the GRAS status of PTS solubilizer for addition to dietary supplements and supplemented beverages, May 2006, available at http://www.accessdata.fda.gov/scripts/fcn/gras_notices/612858a.pdf.*

Egger-Heigold, The effect of excipients on pharmacokinetic parameters of parenteral drugs, 2005, available at http://edoc.unibas.ch/293/1/DissB_7289.pdf.*

U.S. Appl. No. 13/333,179, filed Dec. 2011, Koya et al.*
U.S. Appl. No. 13/642,275, filed Oct. 2012, Nagai et al.*
U.S. Appl. No. 13/273,807, filed Oct. 2011, Koya et al.*
U.S. Appl. No. 12/934,903, filed Sep. 2010, Chen et al.*
U.S. Appl. No. 12/692,895, filed Jan. 2010, Koya et al.*
U.S. Appl. No. 12/310,303, filed Feb. 2009, Koya et al.*
International Search Report and Written Opinion issued in PCT/US2008/012613 on Mar. 22, 2010.

M. Mohan et al., Synthesis, Characterization and Antitumor Properties of Some Metal Complexes of 2,6-Diacetylpyridine Bis(N4-azacyclic Thiosemicarbazones), *J. Inorganic Biochem.* 34, 41-54 (1998).

G. F. de Sousa et al., "Structural and Spectral Studies of a Heterocyclic N(4)-Substituted Bis(thiosemicarbazone), $H_2$2,6Achexim $H_2O$, Its Heptacoordinated Tin(IV) Complex [$Bu_2$Sn(2,6Achexim)], and Its Binuclear Zinc(II) Complex [Zn(2,6Achexim)]$_2$", *Polyhedron*, 19, 841-847 (2000).

Yusupov, V.G. et al., "Copper(II) Complexes with Benzoyl-, thiobenzoylhydrazones and thiosemicarbazones of diacetyl and 1,1-diacetylcyclopropane", Koordinatsionnaya Khimiya 16(10), 1350-1354 (1990).

* cited by examiner

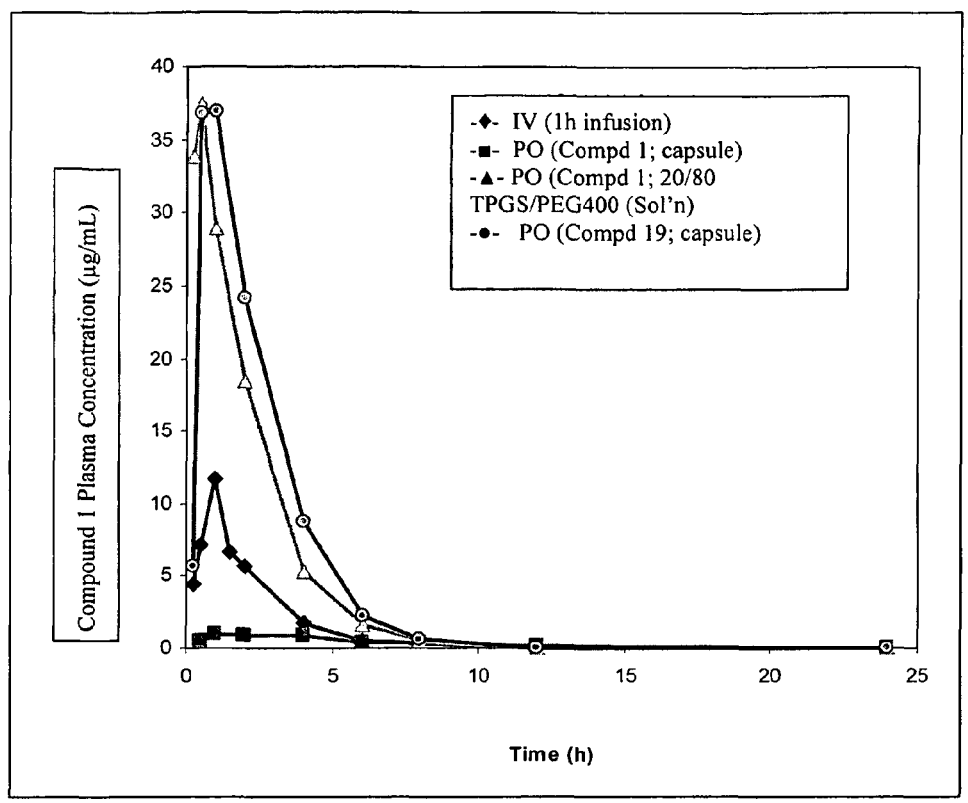
Representative plasma concentration of compounds of the invention vs. time profiles in dog: IV 10 mg/kg; PO 50 mg/kg

ORAL FORMULATIONS OF BIS(THIOHYDRAZIDE AMIDES)

RELATED APPLICATION

This application is the U.S. National Application of International Application No. PCT/US2008/012613, filed Nov. 7, 2008, which claims the benefit of U.S. Provisional Application No. 61/002,623, filed on Nov. 9, 2007. The entire teachings of the above applications are incorporated herein by reference.

BACKGROUND OF THE INVENTION

Heat shock proteins (HSPs) are found in virtually all prokaryotic and eukaryotic cells where they support folding of nascent polypeptides, prevent protein aggregation, and assist transport of other proteins across membranes. The proteins in the Hsp70 family (referred to collectively as "Hsp70") play a dual role of protecting cells from lethal damage after environmental stress, on the one hand, and targeting cells for immune mediated cytolytic attack on the other hand. Increased expression of Hsp70 in the cytoplasma is known to protect a broad range of cells under stress by preventing the misfolding, aggregation and denaturation of cytoplasmic proteins and inhibiting various apoptotic pathways. Mosser, et al., *Mol Cell Biol.*, 2000 October; 20(19): 7146-7159; Yenari, *Adv. Exp. Med. Biol.*, 2002, 513, 281-299; Kiang & Tsokos, *Pharmacol Ther.*, 1998; 80(2):182-201. However, membrane-bound Hsp70 provides a target structure for cytolytic attack mediated by natural killer cells.

Cells can experience stress due to temperature; injury (trauma); genetic disease; metabolic defects; apoptosis; infection; toxins; radiation; oxidants; excess/lack of nutrients or metabolic products; and the like. For example, it is known in the art that cells damaged in the following variety of medical conditions can experience a protective effect in response to Hsp70.

Protein misfolding/aggregation conditions resulting in neurodegeneration include Alzheimers' disease (Zhang, et al., *J. Neuroscience*, 2004, 24(23), 5315-5321; Klettner, *Drug News Perspect*, 2004, 17(5), 299-306); Huntington's disease (Klettner, ibid); Parkinson's disease (Auluck, et al., *Science*, 2002, 295(5556), 865-868); and the like. Other neurodegenerative conditions include spinal/bulbar muscular atrophy (Sobue, *Nihon Shinkei Seishin Yakurigaku Zasshi*, 2001, 21(1), 21-25); and familial amyotrophic lateral sclerosis (Howland, et al., *Proc Nat Acad Sci USA*, 2002, 99(3), 1604-1609; Sobue, ibid; Vleminck, et al., *J. Neuropathol. Exp. Neurol.*, 2002, 61(11), 968-974).

Ischemia and associated oxidative damage affects diverse tissues including: neurons and glia (Carmel, et al., *Exp. Neurol.*, 2004, 185(1) 81-96; Renshaw & Warburton, *Front Biosci.*, 2004, 9, 110-116; Yenari, *Adv. Exp. Med. Biol.*, 2002, 513, 281-299; Kelly & Yenari, *Curr. Res. Med. Opin.*, 2002, 18 Sup. 2, s55-60; Lee, et al., *Exp. Neurol.*, 2001, 170(1), 129-139; Klettner, ibid; Klettner & Herdegen, *Br. J. Pharmacol.*, 2003, 138(5), 1004-1012); cardiac muscle (Marber, M. S., et al., *J. Clin. Invest.*, (1995) 95:1446-1456; Plumier, J. C., et al., *J. Clin. Invest.*, (1995) 95:1854-1860; Radford, N. B., et al., *Proc. Natl. Acad. Sci. USA*, (1996), 93(6): 2339-2342; Voss, et al., *Am. J. Physiol. Heart Circ. Physiol.*, 2003, 285: H687-H692); liver tissue (Doi, et al., *Hepatogastroenterology*, 2001 March-April; 48(38):533-40; Gao, et al., *World J. Gastroenterol.*, 2004; 10(7):1019-1027); skeletal muscle (Lepore et al., *Cell Stress & Chaperones*, 2001, 6(2), 93-96); kidney tissue (Chen, et al., *Kidney Int.*, 1999; 56: 1270-1273; Beck, et al., *Am. J. Physiol. Renal Physiol.*, 2000, 279: F203-F215); pulmonary tissue (Hiratsuka, et al., *J. Heart Lung Transplant*, 1998 December; 17(12):1238-46); pancreatic tissue (Bellmann, et al., *J. Clin. Invest.*, 1995 June; 95(6): 2840-2845), and the like.

Seizure conditions that damage neurons include, e.g., epileptic seizure (Yenari, ibid; Blondeau, et al., *Neuroscience*, 2002, 109(2), 231-241); or chemically induced seizure (Tsuchiya, et al., *Neurosurgery*, 2003, 53(5), 1179-1187).

Thermal stresses include hyperthermia conditions such as fever, heat stroke, and the like (Barclay & Robertson, *J. Neurobiol.*, 2003 56(4), 360-271; Sato, et al., *Brain Res.*, 1996, 740(1-2), 117-123); and hypothermia (Kandor & Goldberg, *Proc. Natl. Acad. Sci. USA*, 1997 May 13; 94(10): 4978-4981).

Aging includes conditions such as atherosclerosis which affects smooth muscle cells (Minowada, G. & Welch, W. J., *J. Clin. Invest.*, (1995), 95:3-12; Johnson, A. J., et al., *Arterio. Thromb. Vasc. Biol.*, (1995), 15(1):27-36).

Other conditions include radiation damage, e.g., from ultraviolet light to tissues such as murine fibroblasts (Simon, M. M., et al., *J. Clin. Res.*, (1995), 95(3): 926-933), and light damage to retinal cells (Yu, et al, *Molecular Vision*, 2001; 7:48-56).

Trauma includes, for example, mechanical injury, e.g., pressure damage to retinal ganglions in glaucoma (Ishii, et al., *Invest. Opthalmol. Vis. Sci.*, 2003, 44(5), 1982-1992).

Toxic conditions include doses of chemicals or biochemicals, for example, methamphetamine (Malberg & Seiden, Poster "MDMA Administration Induces Expression of HSP70 in the Rat Brain" Society for Neuroscience Annual Meeting, New Orleans, La., Oct. 25-30, 1997); antiretroviral HIV therapeutics (Keswani, et al., *Annals Neurology*, 2002, 53(1), 57-64); heavy metals, amino acid analogs, chemical oxidants, ethanol, glutamate, and other toxins (Ashburner, M. & Bonner, J. J., *Cell*, (1979) 17:241-254; Lindquist, S., *Ann. Rev. Biochem.*, (1986) 55:1151-1191; Craig, E. A., *Crit. Rev. Biochem.* (1985), 18(3):239-280; MORIMOTO, et al., THE BIOLOGY OF HEAT SHOCK PROTEINS AND MOLECULAR CHAPERONE, (Cold Spring Harbor Laboratory Press 1994), 417-455); and the like.

Cystic fibrosis is a genetic disorder which results from a mutation in a single glycoprotein called the cystic fibrosis transmembrane conductance regulator (CFTR). As a result of the mutation, post-translational processing of CFTR cannot proceed correctly and the glycoprotein fails to be delivered to the cell membrane. Induction of Hsp70 has been shown to overcome this defective processing and results in functional CFTR protein on the cell surface (Choo-Kang & Zeitlin, *Am. J. Physiol. Lung Cell Mol. Physiol.*, (2001), 281:L58-L68).

Therefore, there is a need for new methods of increasing expression of Hsp70 in order to treat disorders responsive to Hsp70.

Extracellular Hsp70 and membrane bound Hsp70 have been shown to play key roles in activation of the innate immune system. Monocytes have been shown to secrete proinflammatory cytokines in response to soluble Hsp70 protein and membrane bound Hsp70 has been shown to provide a target structure for cytolytic attack by natural killer cell.

Natural killer (NK) cells, a type of white blood cell, are known to be an important component of the body's immune system. Because the defining function of NK cells is spontaneous cytotoxicity without prior immunization, NK cells can be the first line of defense in the immune system, and are believed to play a role in attacking cancer cells and infectious diseases. Many conditions, such as immunodeficiency diseases, aging, toxin exposure, endometriosis, and the like can leave subjects with lowered NK cell activity or dysfunctional NK cells.

For example, subjects can have decreased or deficient NK cell activity, in conditions such as chronic fatigue syndrome (chronic fatigue immune dysfunction syndrome) or Epstein-Barr virus, post viral fatigue syndrome, post-transplantation syndrome or host-graft disease, exposure to drugs such as anticancer agents or nitric oxide synthase inhibitors, natural aging, and various immunodeficiency conditions such as severe combined immunodeficiency, variable immunodeficiency syndrome, and the like. (Caligiuri, et al., *J. of Immunology*, 1987; 139: 3306-13; Morrison, et al., *Clinical and Experimental Immunology*, 1991; 83: 441-6; Klingemann, *Biology of Blood and Marrow Transplantation*, 2000, 6:90-99; Ruggeri, et al., *Best Pract Res Clin Haematol.*, 2004, 17(3):427-38; Cifone, et al., *Int. Immunopharmacol.*, 2001, 1(8):1513-24; Plackett, et al., *J. Leukoc. Biol.*, 2004 August, 76(2):291-9; Alpdogan & van den Brink, *Trends Immunol.*, 2005 January, 26(1):56-64; Heusel & Ballas Z K, *Curr. Opin. Pediatr.*, 2003 December, 15(6):586-93; Hacein-Bey-Abina, et al., *Int. J. Hematol.*, 2002 November, 76(4):295-8; Baumert, et al., *Immun Infekt.*, 1992 July, 20(3):73-5).

NK cells are known to have activity against a wide range of infectious pathogens such as bacteria, viruses, fungi, protozoan parasites, combined infections, e.g., combined bacterial/viral infections, and the like. NK cells are believed to be particularly important in combating intracellular infections where the pathogens replicate in the subjects cells, e.g., a substantial fraction of viruses and many other pathogens that can form intracellular infections.

For example, a wide range of fungal infections are reported to be targeted by NK cells such as *Cryptococcus neoformans, dermatophytes*, e.g., *Trichophyton rubrum, Candida albicans, Coccidioides immitis, Paracoccidioides brasiliensis*, or the like (Hidore, et al., *Infect. Immun.*, 1991 April, 59(4): 1489-99; Akiba, et al., *Eur. J. Dermatol.*, 2001 January-February, 11(1):58-62; Mathews & Witek-Janusek, *J. Med. Microbiol.*, 1998 November, 47(11):1007-14; Ampel, et al., *Infect. Immun.*, 1992 October, 60(10):4200-4; Jimenez & Murphy, *Infect. Immun.*, 1984 November, 46(2):552-8.)

Also targeted by NK cells are bacteria, especially intracellular bacteria, e.g., *Mycobacterium tuberculosis, Mycobacterium avium, Listeria monocytogenes*, many different viruses, such as human immunodeficiency virus, herpesviruses, hepatitis, and the like, and viral/bacterial co-infection (Esin et al., *Clin. Exp. Immunol.*, 1996 June, 104(3):419-25; Kaufmann, *Annu. Rev. Immunol.*, 1993, 11:129-63; See et al., *Scand. J. Immunol.*, 1997 September, 46(3):217-24; Brenner et al., *J. Leukoc. Biol.*, 1989 July, 46(1):75-83; Kottilil S., *Indian J. Exp. Biol.*, 2003 November, 41(11):1219-25; Herman & Koziel, *Clin. Gastroenterol. Hepatol.*, 2004 December, 2(12):1061-3; Beadling & Slifka, *Curr. Opin. Infect. Dis.*, 2004 June, 17(3):185-91).

In addition, NK cells combat protozoal infections including toxoplasmosis, trypanosomiasis, leishmaniasis and malaria, especially intracellular infections (Korbel, et al., *Int. J. Parasitol.*, 2004 December, 34(13-14):1517-28; Ahmed & Mehlhorn, *Parasitol. Res.*, 1999 July, 85(7):539-49; Osman, et al., *Dig. Surg.*, 1998, 15(4):287-96; Gazzinelli, et al., *Infect. Agents Dis.*, 1993 June, 2(3):139-49; Askonas & Bancroft, *Philos. Trans. R. Soc. Lond. B: Biol. Sci.*, 1984 Nov. 13, 307(1131):41-9; Allison & Eugui, *Annu. Rev. Immunol.*, 1983; 1:361-92).

NK cells have been shown to play a role in attacking cancer cells that present membrane bound Hsp70. It is believed that membrane bound Hsp70 binds to CD94 receptors on the surface of NK cells to cause them to produce and secrete high amounts of the enzyme granzyme B which is thought to enter the tumor cell via interaction with membrane bound Hsp70 and induce apoptosis (Radons & Multhoff, Exerc. *Immunol. Rev.*, (2005), 11:17-33). Therefore, there is an urgent need for effective treatments for increasing NK cell activity for the treatment of cancer and other disorders that respond to NK induction.

SUMMARY OF THE INVENTION

It has been reported in U.S. Pat. Nos. 6,800,660, 6,762,204, 7,037,940, 7,001,923, and 6,924,312 that certain bis(thio-hydrazide amide) compounds significantly enhance the anticancer activity of taxol and taxol analogs. The entire teachings of these patents are incorporated by reference herein in their entirety. Disclosed herein are oral formulations of bis (thio-hydrazide amide) compounds or a pharmaceutically acceptable salt thereof.

One embodiment of the present invention is an oral formulation of a compound represented by Structural Formula I:

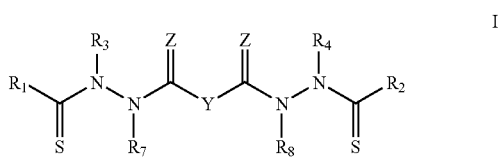

or a pharmaceutically acceptable salt thereof, wherein:

Y is a covalent bond or an optionally substituted straight chained hydrocarbyl group, or, Y, taken together with both >C=Z groups to which it is bonded, is an optionally substituted aromatic group;

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic ring optionally fused to an aromatic ring;

$R_7$-$R_8$ are independently —H, an optionally substituted aliphatic group, or an optionally substituted aryl group; and each Z is independently O or S.

BRIEF DESCRIPTION OF THE DRAWINGS

FIG. 1 is a graph of the plasma concentration of compounds of the invention vs. time profiles in dog: IV 10 mg/kg; PO 50 mg/k.

DETAILED DESCRIPTION OF THE INVENTION

The present invention relates to oral formulations of bis (thio-hydrazide amides) represented by Structural Formula I and pharmaceutically acceptable salts and solvates of the compounds represented by Structural Formula I.

In one embodiment, the oral formulation may be administered in a form selected from the group consisting of a tablet, a pill, a powder, a granule, a solution, an emulsion, a suspension, syrup, an elixir, or a capsule.

In one embodiment, the oral formulation comprises a compound of the invention and a GRAS excipient.

In one embodiment, the oral formulation comprises a compound of the invention in the form of a nanoparticle formulation.

In one embodiment, the oral formulation comprises a compound of the invention and a polymeric suspending agent.

In one embodiment, the oral formulation comprises a compound of the invention and a phospholipid emulsifier.

In one embodiment, the oral formulation comprises a compound of the invention and a cyclodextrin or its derivative.

In one aspect, the oral formulation contains in the range of 5 to 10 mg/mL of a compound of the invention.

In one embodiment, the % F of the oral formulation is at least 5%. In one aspect, the % F is at least 10%. In one aspect, the % F is at least 15%. In one aspect, the % F is at least 20%. In one aspect, the % F is at least 25%. In one aspect, the % F is at least 30%. In one aspect, the % F is at least 35%. In one aspect, the % F is at least 40%. In one aspect, the % F is at least 45%. In one aspect, the % F is at least 50%. In one aspect, the % F is at least 55%. In one aspect, the % F is at least 60%. In one aspect, the % F is at least 65%. In one aspect, the % F is at least 70%. In one aspect, the % F is at least 75%. In one aspect, the % F is at least 80%.

In one embodiment, Y in Structural Formula I is a covalent bond, —C($R_5R_6$)—, trans-(CH═CH)—, cis-(CH═CH)— or —(C≡C)— group, preferably —C($R_5R_6$)—. $R_1$-$R_4$ are as described above for Structural Formula I. $R_5$ and $R_6$ are each independently —H, an aliphatic or substituted aliphatic group, or one of $R_5$ and $R_6$ is —H, and the other is an optionally substituted aryl group, or, $R_5$ and $R_6$, taken together, are an optionally substituted $C_2$-$C_6$ alkylene group.

In specific embodiments, Y taken together with both >C═Z groups to which it is bonded, is an optionally substituted aromatic group. In this instance, certain bis(thio-hydrazide amides) are represented by Structural Formula II:

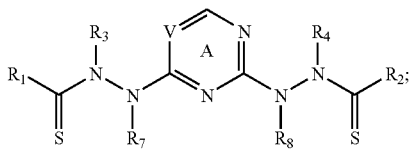

II or a pharmaceutically acceptable salt thereof, wherein Ring A is substituted or unsubstituted and V is —CH— or —N—. The other variables in Structural Formula II are as described herein for Structural Formula I or IIIa.

In particular embodiments, the bis(thio-hydrazide amides) are represented by Structural Formula IIIa:

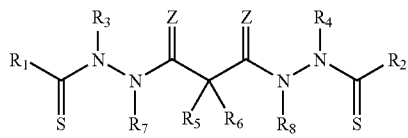

IIIa or a pharmaceutically acceptable salt thereof, wherein $R_1$-$R_8$ are as described above for Structural Formula I.

In Structural Formulae I-IIIa, $R_1$ and $R_2$ are the same or different and/or $R_3$ and $R_4$ are the same or different; preferably, $R_1$ and $R_2$ are the same and $R_3$ and $R_4$ are the same. In Structural Formulas I and IIIa, each Z is preferably O. Typically in Structural Formulas I and IIIa, each Z is O; $R_1$ and $R_2$ are the same; and $R_3$ and $R_4$ are the same. More preferably, for Structural Formula IIIa, each Z is O; $R_1$ and $R_2$ are the same; $R_3$ and $R_4$ are the same, and $R_7$ and $R_8$ are the same.

In other embodiments, the bis(thio-hydrazide amides) are represented by Structural Formula IIIa: $R_1$ and $R_2$ are each an optionally substituted aryl group, preferably an optionally substituted phenyl group; $R_3$ and $R_4$ are each an optionally substituted aliphatic group, preferably an alkyl group optionally substituted with —OH, halogen, phenyl, benzyl, pyridyl, or $C_1$-$C_8$ alkoxy; and $R_5$ and $R_6$ are as described above, but one of $R_5$ and $R_6$ is preferably —H and the other is preferably —H, an aliphatic or substituted aliphatic group.

Alternatively, $R_1$ and $R_2$ are each an optionally substituted aryl group; $R_3$ and $R_4$ are each an optionally substituted aliphatic group; one of $R_5$ and $R_6$ is —H and the other is —H, an aliphatic or substituted aliphatic group. Preferably, $R_1$ and $R_2$ are each an optionally substituted aryl group; $R_3$ and $R_4$ are each an alkyl group optionally substituted with —OH, halogen, phenyl, benzyl, pyridyl, or $C_1$-$C_8$ alkoxy; and one of $R_5$ and $R_6$ is —H and the other is —H or methyl. Even more preferably, $R_1$ and $R_2$ are each an optionally substituted phenyl group, preferably optionally substituted with —OH, halogen, $C_{1-4}$ alkyl or $C_1$-$C_4$ alkoxy; $R_3$ and $R_4$ are each methyl or ethyl optionally substituted with —OH, halogen or $C_1$-$C_4$ alkoxy; and one of $R_5$ and $R_6$ is —H and the other is —H or methyl. Suitable substituents for an aryl group represented by $R_1$ and $R_2$ and an aliphatic group represented by $R_3$, $R_4$, $R_5$ and $R_6$ as described for any above embodiment are as described below for aryl and aliphatic groups.

In another embodiment, the bis(thio-hydrazide amides) are represented by Structural Formula IIIa: $R_1$ and $R_2$ are each an optionally substituted aliphatic group, preferably a $C_3$-$C_8$ cycloalkyl group optionally substituted with at least one alkyl group, more preferably cyclopropyl or 1-methylcyclopropyl; $R_3$ and $R_4$ are as described above for Structural Formula I, preferably both an optionally substituted alkyl group; and $R_5$ and $R_6$ are as described above, but one of $R_5$ and $R_6$ is preferably —H and the other is preferably —H, an aliphatic or substituted aliphatic group, more preferably —H or methyl.

Alternatively, the bis(thio-hydrazide amides) are represented by Structural Formula IIIa: $R_1$ and $R_2$ are each an optionally substituted aliphatic group; $R_3$ and $R_4$ are as described above for Structural Formula I, preferably both an optionally substituted alkyl group; and one of $R_5$ and $R_6$ is —H and the other is —H or an optionally substituted aliphatic group. More preferably, $R_1$ and $R_2$ are both a $C_3$-$C_8$ cycloalkyl group optionally substituted with at least one alkyl group; $R_3$ and $R_4$ are both an alkyl group optionally substituted with —OH, halogen, phenyl, benzyl, pyridyl, or $C_1$-$C_8$ alkoxy; and one of $R_5$ and $R_6$ is —H and the other is —H or methyl. Even more preferably, $R_1$ and $R_2$ are both cyclopropyl or 1-methylcyclopropyl; $R_3$ and $R_4$ are both an alkyl group, preferably methyl or ethyl optionally substituted with —OH, halogen or $C_1$-$C_4$ alkoxy; and one of $R_5$ and $R_6$ is —H and the other is —H or methyl.

In particular embodiments, the bis(thio-hydrazide amides) are represented by Structural Formula IIIb:

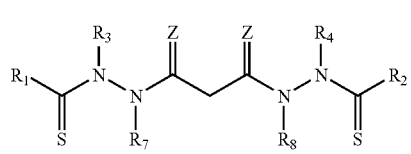

IIIb or a pharmaceutically acceptable salt thereof, wherein $R_1$, $R_2$, $R_3$, $R_4$, $R_7$, $R_8$, and Z are as defined above for Structural Formula IIIa.

In specific embodiments, the bis(thio-hydrazide amides) are represented by Structural Formula IVa:

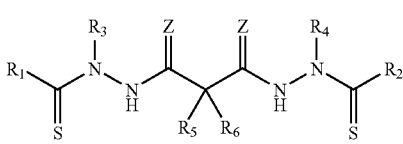

or a pharmaceutically acceptable salt thereof, wherein: $R_1$ and $R_2$ are both phenyl, $R_3$ and $R_4$ are both methyl, and $R_5$ and $R_6$ are both —H; $R_1$ and $R_2$ are both phenyl, $R_3$ and $R_4$ are both ethyl, and $R_5$ and $R_6$ are both —H; $R_1$ and $R_2$ are both 4-cyanophenyl, $R_3$ and $R_4$ are both methyl, $R_5$ is methyl, and $R_6$ is —H; $R_1$ and $R_2$ are both 4-methoxyphenyl, $R_3$ and $R_4$ are both methyl, and $R_5$ and $R_6$ are both —H; $R_1$ and $R_2$ are both phenyl, $R_3$ and $R_4$ are both methyl, $R_5$ is methyl, and $R_6$ is —H; $R_1$ and $R_2$ are both phenyl, $R_3$ and $R_4$ are both ethyl, $R_5$ is methyl, and $R_6$ is —H; $R_1$ and $R_2$ are both 4-cyanophenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, $R_5$ is methyl, and $R_6$ is —H; $R_1$ and $R_2$ are both 3-cyanophenyl, $R_3$ and $R_4$ are both methyl, and $R_5$ and $R_6$ are both —H; $R_1$ and $R_2$ are both 3-fluorophenyl, $R_3$ and $R_4$ are both methyl, and $R_5$ and $R_6$ are both —H; $R_1$ and $R_2$ are both 4-chlorophenyl, $R_3$ and $R_4$ are both methyl, $R_5$ is methyl, and $R_6$ is —H; $R_1$ and $R_2$ are both 2-methoxyphenyl, $R_3$ and $R_4$ are both methyl, and $R_5$ and $R_6$ are both —H; $R_1$ and $R_2$ are both 3-methoxyphenyl, $R_3$ and $R_4$ are both methyl, and $R_5$ and $R_6$ are both —H; $R_1$ and $R_2$ are both 2,3-dimethoxyphenyl, $R_3$ and $R_4$ are both methyl, and $R_5$ and $R_6$ are both —H; $R_1$ and $R_2$ are both 2,3-dimethoxyphenyl, $R_3$ and $R_4$ are both methyl, $R_5$ is methyl, and $R_6$ is —H; $R_1$ and $R_2$ are both 2,5-difluorophenyl, $R_3$ and $R_4$ are both methyl, and $R_5$ and $R_6$ are both —H; $R_1$ and $R_2$ are both 2,5-difluorophenyl, $R_3$ and $R_4$ are both methyl, $R_5$ is methyl, and $R_6$ is —H; $R_1$ and $R_2$ are both 2,5-dichlorophenyl, $R_3$ and $R_4$ are both methyl, and $R_5$ and $R_6$ are both —H; $R_1$ and $R_2$ are both 2,5-dimethylphenyl, $R_3$ and $R_4$ are both methyl, and $R_5$ and $R_6$ are both —H; $R_1$ and $R_2$ are both cyclopropyl, $R_3$ and $R_4$ are both methyl, and $R_5$ and $R_6$ are both —H; $R_1$ and $R_2$ are both cyclopropyl, $R_3$ and $R_4$ are both ethyl, and $R_5$ and $R_6$ are both —H; $R_1$ and $R_2$ are both cyclopropyl, $R_3$ and $R_4$ are both methyl, $R_5$ is methyl, and $R_6$ is —H; $R_1$ and $R_2$ are both 1-methylcyclopropyl, $R_3$ and $R_4$ are both methyl, and $R_5$ and $R_6$ are both —H; $R_1$ and $R_2$ are both 1-methylcyclopropyl, $R_3$ and $R_4$ are both methyl, $R_5$ is methyl and $R_6$ is —H; $R_1$ and $R_2$ are both 1-methylcyclopropyl, $R_3$ and $R_4$ are both methyl, $R_5$ is ethyl, and $R_6$ is —H; $R_1$ and $R_2$ are both 1-methylcyclopropyl, $R_3$ and $R_4$ are both methyl, $R_5$ is n-propyl, and $R_6$ is —H; $R_1$ and $R_2$ are both 1-methylcyclopropyl, $R_3$ and $R_4$ are both methyl, and $R_5$ and $R_6$ are both methyl; $R_1$ and $R_2$ are both 1-methylcyclopropyl, $R_3$ and $R_4$ are both ethyl, and $R_5$ and $R_6$ are both —H; $R_1$ and $R_2$ are both 1-methylcyclopropyl, $R_3$ is methyl, $R_4$ is ethyl, and $R_5$ and $R_6$ are both —H; $R_1$ and $R_2$ are both 2-methylcyclopropyl, $R_3$ and $R_4$ are both methyl, and $R_5$ and $R_6$ are both —H; $R_1$ and $R_2$ are both 2-phenylcyclopropyl, $R_3$ and $R_4$ are both methyl, and $R_5$ and $R_6$ are both —H; $R_1$ and $R_2$ are both 1-phenylcyclopropyl, $R_3$ and $R_4$ are both methyl, and $R_5$ and $R_6$ are both —H; $R_1$ and $R_2$ are both cyclobutyl, $R_3$ and $R_4$ are both methyl, and $R_5$ and $R_6$ are both —H; $R_1$ and $R_2$ are both cyclopentyl, $R_3$ and $R_4$ are both methyl, and $R_5$ and $R_6$ are both —H; $R_1$ and $R_2$ are both cyclohexyl, $R_3$ and $R_4$ are both methyl, and $R_5$ and $R_6$ are both —H; $R_1$ and $R_2$ are both cyclohexyl, $R_3$ and $R_4$ are both phenyl, and $R_5$ and $R_6$ are both —H; $R_1$ and $R_2$ are both methyl, $R_3$ and $R_4$ are both methyl, and $R_5$ and $R_6$ are both —H; $R_1$ and $R_2$ are both methyl, $R_3$ and $R_4$ are both t-butyl, and $R_5$ and $R_6$ are both —H; $R_1$ and $R_2$ are both methyl, $R_3$ and $R_4$ are both phenyl, and $R_5$ and $R_6$ are both —H; $R_1$ and $R_2$ are both t-butyl, $R_3$ and $R_4$ are both methyl, and $R_5$ and $R_6$ are both —H; $R_1$ and $R_2$ are ethyl, $R_3$ and $R_4$ are both methyl, and $R_5$ and $R_6$ are both —H; or $R_1$ and $R_2$ are both n-propyl, $R_3$ and $R_4$ are both methyl, and $R_5$ and $R_6$ are both —H.

In one embodiment, when $R_1$ and $R_2$ are both an unsubstituted phenyl; $R_3$ and $R_4$ are both methyl, and either $R_5$ or $R_6$ is —H, then the other of $R_5$ and $R_6$ is other than —H.

In specific embodiments, the bis(thio-hydrazide amides) are represented by Structural Formula V:

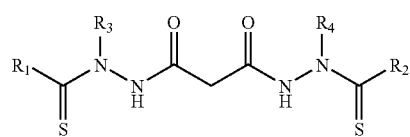

or a pharmaceutically acceptable salt thereof, wherein: $R_1$ and $R_2$ are both phenyl, and $R_3$ and $R_4$ are both o-$CH_3$-phenyl; $R_1$ and $R_2$ are both o-$CH_3C(O)O$-phenyl, and $R_3$ and $R_4$ are phenyl; $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both phenyl, and $R_3$ and $R_4$ are both n-propyl; $R_1$ and $R_2$ are both p-cyanophenyl, and $R_3$ and $R_4$ are both methyl; $R_1$ and $R_2$ are both p-nitro phenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both n-butyl; $R_1$ and $R_2$ are both p-chlorophenyl, and $R_3$ and $R_4$ are both methyl; $R_1$ and $R_2$ are both 3-nitrophenyl, and $R_3$ and $R_4$ are both methyl; $R_1$ and $R_2$ are both 3-cyanophenyl, and $R_3$ and $R_4$ are both methyl; $R_1$ and $R_2$ are both 3-fluorophenyl, and $R_3$ and $R_4$ are both methyl; $R_1$ and $R_2$ are both 2-furanyl, and $R_3$ and $R_4$ are both phenyl; $R_1$ and $R_2$ are both 2-methoxyphenyl, and $R_3$ and $R_4$ are both methyl; $R_1$ and $R_2$ are both 3-methoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2-methoxy-5-chlorophenyl, and $R_3$ and $R_4$ are both ethyl; $R_1$ and $R_2$ are both 2,5-difluorophenyl, and $R_3$ and $R_4$ are both methyl; $R_1$ and $R_2$ are both 2,5-dichlorophenyl, and $R_3$ and $R_4$ are both methyl; $R_1$ and $R_2$ are both 2,5-dimethylphenyl, and $R_3$ and $R_4$ are both methyl; $R_1$ and $R_2$ are both 2-methoxy-5-chlorophenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both 2-ethylphenyl; $R_1$ and $R_2$ are both 2-methyl-5-pyridyl, and $R_3$ and $R_4$ are both methyl; or $R_1$ is phenyl; $R_2$ is 2,5-dimethoxyphenyl, and $R_3$ and $R_4$ are both methyl; $R_1$ and $R_2$ are both methyl, and $R_3$ and $R_4$ are both p-$CF_3$-phenyl; $R_1$ and $R_2$ are both methyl, and $R_3$ and $R_4$ are both o-$CH_3$-phenyl; $R_1$ and $R_2$ are both —$(CH_2)_3COOH$; and $R_3$ and $R_4$ are both phenyl; $R_1$ and $R_2$ are both represented by the following structural formula:

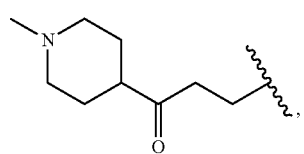 [SMILES: *CCC(=O)C1CCN(C)CC1]

and $R_3$ and $R_4$ are both phenyl; $R_1$ and $R_2$ are both n-butyl, and $R_3$ and $R_4$ are both phenyl; $R_1$ and $R_2$ are both n-pentyl, $R_3$ and $R_4$ are both phenyl; $R_1$ and $R_2$ are both methyl, and $R_3$ and $R_4$ are both 2-pyridyl; $R_1$ and $R_2$ are both cyclohexyl, and $R_3$ and $R_4$ are both phenyl; $R_1$ and $R_2$ are both methyl, and $R_3$ and $R_4$ are both 2-ethylphenyl; $R_1$ and $R_2$ are both methyl, and $R_3$ and $R_4$ are both 2,6-dichlorophenyl; $R_1$-$R_4$ are all methyl; $R_1$ and $R_2$ are both methyl, and $R_3$ and $R_4$ are both t-butyl; $R_1$ and $R_2$ are both ethyl, and $R_3$ and $R_4$ are both methyl; $R_1$ and $R_2$ are both t-butyl, and $R_3$ and $R_4$ are both methyl; $R_1$ and $R_2$ are both cyclopropyl, and $R_3$ and $R_4$ are both methyl; $R_1$ and $R_2$ are both cyclopropyl, and $R_3$ and $R_4$ are both ethyl; $R_1$ and $R_2$ are both 1-methylcyclopropyl, and $R_3$ and $R_4$ are both methyl; $R_1$ and $R_2$ are both 2-methylcyclopropyl, and $R_3$ and $R_4$ are both methyl; $R_1$ and $R_2$ are both 1-phenylcyclopropyl, and $R_3$ and $R_4$ are both methyl; $R_1$ and $R_2$ are both 2-phenylcyclopropyl, and $R_3$ and $R_4$ are both methyl; $R_1$ and $R_2$ are both cyclobutyl, and $R_3$ and $R_4$ are both methyl; $R_1$ and $R_2$ are both cyclopentyl, and $R_3$ and $R_4$ are both methyl; $R_1$ is cyclopropyl, $R_2$ is phenyl, and $R_3$ and $R_4$ are both methyl.

One example of a bis(thio-hydrazide amide) of the invention is compound (1), or a pharmaceutically acceptable salt thereof Compound (1)

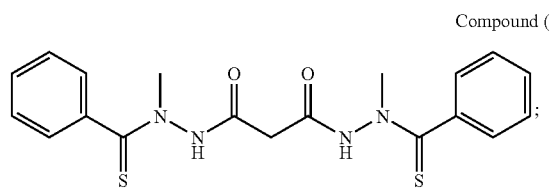

Preferred examples of bis(thio-hydrazide amides) include Compounds (2)-(18) and pharmaceutically acceptable salts thereof:

Compound (2)

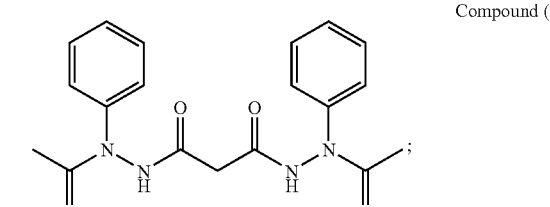

Compound (3)

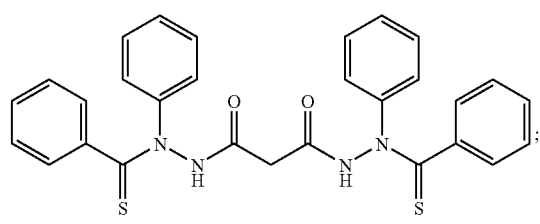

Compound (4)

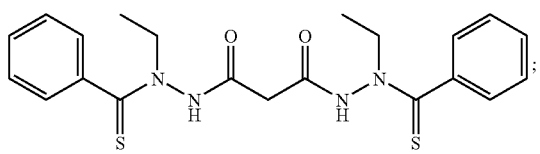

Compound (5)

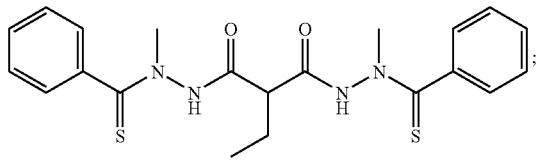

Compound (6)

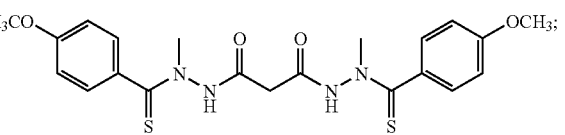

Compound (7)

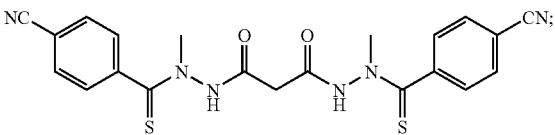

Compound (8)

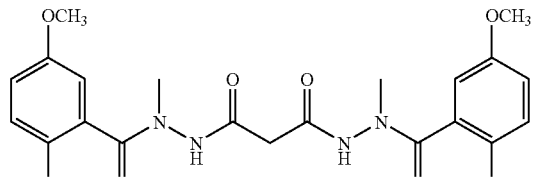

Compound (9)

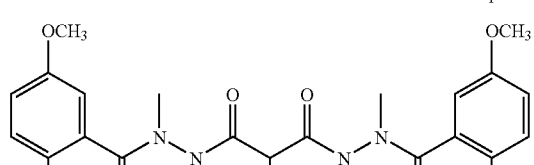

Compound (10)

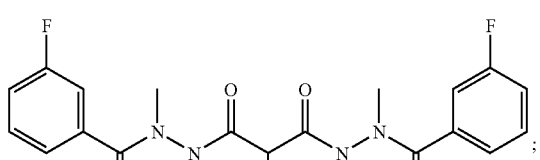

Compound (11)

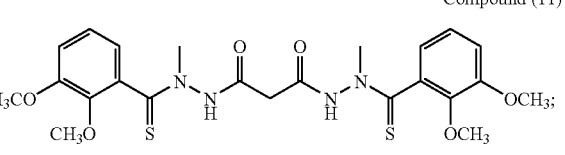

-continued

Compound (12)
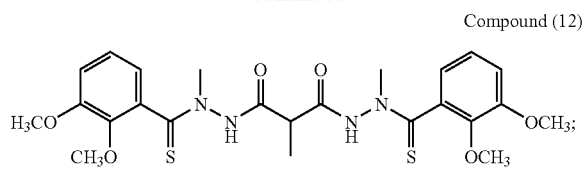

Compound (13)
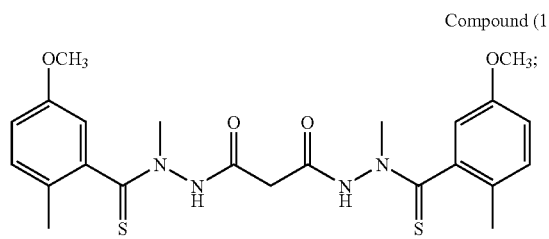

Compound (14)
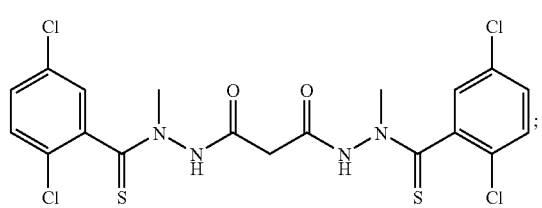

Compound (15)
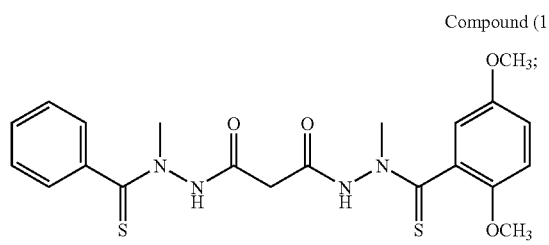

Compound (16)
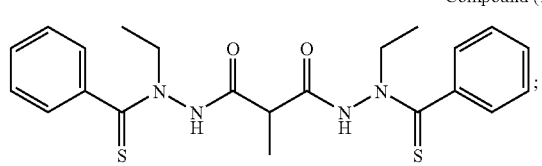

Compound (17)
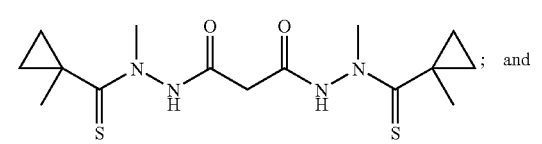
; and

Compound (18)
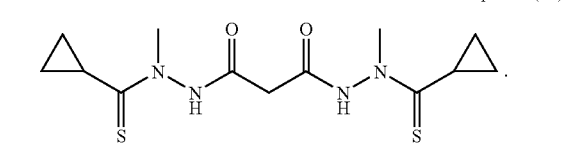

Another embodiment of the present invention is an oral formulation of a disalt compound represented by the following Structural Formula (IA), and its tautomeric forms:

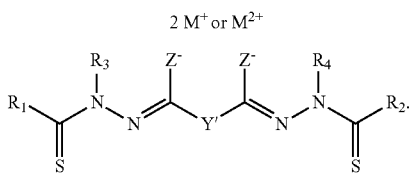
(IA)

Y' is a covalent bond or a substituted or unsubstituted straight chained hydrocarbyl group. $R_1$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring. Each Z is independently O or S. $M^+$ is a pharmaceutically acceptable cation with a +1 charge and $M^{2+}$ is a pharmaceutically acceptable cation with a +2 charge.

"Pharmaceutically acceptable cation" means that the cation is suitable for administration to a subject. Examples of $M^+$ or $M^{2+}$ include $Li^+$, $Na^+$, $K^+$, $Mg^{2+}$, $Ca^{2+}$, $Zn^{2+}$, and $NR_4^+$, wherein each R is independently hydrogen, a substituted or unsubstituted aliphatic group (e.g., a hydroxyalkyl group, aminoalkyl group or ammoniumalkyl group) or substituted or unsubstituted aryl group, or two R groups, taken together, form a substituted or unsubstituted non-aromatic heterocyclic ring optionally fused to an aromatic ring. Preferably, the pharmaceutically acceptable cation is $Li^+$, $Na^+$, $K^+$, $NH_3(C_2H_5OH)^+$, $N(CH_3)_3(C_2H_5OH)^+$, arginine, or lysine. More preferably, the pharmaceutically acceptable cation is $Na^+$ or $K^+$. $Na^+$ is even more preferred.

In Structural Formula (IA), each Z is preferably —O. More preferably, each Z is —O; $R_1$ and $R_2$ are the same; and $R_3$ and $R_4$ are the same.

In one embodiment, Y' in Structural Formula (IA) is a covalent bond, —C($R_5R_6$)—, trans-(CH=CH)—, cis-(CH=CH)— or —(C≡C)— group, preferably —C($R_5R_6$)—. $R_1$-$R_4$ are as described above for Structural Formula (IA). $R_5$ and $R_6$ are each independently —H, an aliphatic or substituted aliphatic group, or one of $R_5$ and $R_6$ is —H and the other is a substituted or unsubstituted aryl group, or, $R_5$ and $R_6$, taken together, are a $C_2$-$C_6$ substituted or unsubstituted alkylene group. $M^+$ is as described above.

In a preferred embodiment of the present invention, the bis(thio-hydrazide amide) disalt is represented by Structural Formula (IIA):

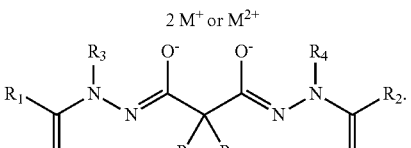
(IIA)

wherein $R_1$-$R_6$ and $M^+$ are as described above for Structural Formula (IA).

In one more preferred embodiment of the present invention, the bis(thio-hydrazide amide) disalt is represented by Structural Formula (IIA) where $R_1$ and $R_2$ are each a substituted or unsubstituted aryl group, preferably a substituted or unsubstituted phenyl group; $R_3$ and $R_4$ are each a substituted or unsubstituted aliphatic group, preferably an alkyl group, more preferably, methyl or ethyl; and $R_5$ and $R_6$ are as described above, but one of $R_5$ and $R_6$ is preferably —H and the other is preferably —H, an aliphatic or substituted aliphatic group.

Preferably, $R_1$ and $R_2$ are each a substituted or unsubstituted aryl group; $R_3$ and $R_4$ are each an alkyl group; and one of $R_5$ and $R_6$ is —H and the other is —H or methyl. Even more preferably, $R_1$ and $R_2$ are each a substituted or unsubstituted phenyl group; $R_3$ and $R_4$ are each methyl or ethyl; and one of $R_5$ and $R_6$ is —H and the other is —H or methyl. Suitable substituents for an aryl group represented by $R_1$ and $R_2$ and an aliphatic group represented by $R_3$, $R_4$ and $R_6$ are as described below for aryl and aliphatic groups.

In one embodiment of the invention, for either Structural Formula (IA) or (IIA), when both $R_1$ and $R_2$ are an unsubstituted phenyl, both $R_3$ and $R_4$ are methyl, and one of $R_5$ and $R_6$ is —H, then the other of $R_5$ and $R_6$ is other than —H.

In a more preferred embodiment of the present invention, the bis(thio-hydrazide amide) disalt is represented by Structural Formula (IIA) where $R_1$ and $R_2$ are each a substituted or unsubstituted aliphatic group, preferably a $C_3$-$C_8$ cycloalkyl group optionally substituted with at least one alkyl group, more preferably cyclopropyl or 1-methylcyclopropyl; $R_3$ and $R_4$ are as described above for Structural Formula (IA), preferably both a substituted or unsubstituted alkyl group; and $R_5$ and $R_6$ are as described above, but one of $R_5$ and $R_6$ is preferably —H and the other is preferably —H, an aliphatic or substituted aliphatic group, more preferably —H or methyl.

Alternatively, the bis(thio-hydrazide amide) disalt is represented by Structural Formula (IIA) wherein $R_1$ and $R_2$ are each a substituted or unsubstituted aliphatic group; $R_3$ and $R_4$ are as described above for Structural Formula (IA), preferably both a substituted or unsubstituted alkyl group; and one of $R_5$ and $R_6$ is —H and the other is —H or an optionally substituted aliphatic group. More preferably, $R_1$ and $R_2$ are both a $C_3$-$C_8$ cycloalkyl group optionally substituted with at least one alkyl group; $R_3$ and $R_4$ are both an alkyl group; and one of $R_5$ and $R_6$ is —H and the other is —H or methyl. Even more preferably, $R_1$ and $R_2$ are both cyclopropyl or 1-methylcyclopropyl; $R_3$ and $R_4$ are both an alkyl group, preferably methyl or ethyl; and one of $R_5$ is and $R_6$ —H and the other is —H or methyl.

The following are specific examples of bis(thio-hydrazide amide) disalts represented by Structural Formula (IIA): $R_1$ and $R_2$ are both phenyl; $R_3$ and $R_4$ are both methyl; $R_5$ is —H, and $R_6$ is ethyl; $R_1$ and $R_2$ are both phenyl; $R_3$ and $R_4$ are both phenyl, and $R_5$ and $R_6$ are both methyl; $R_1$ and $R_2$ are both 2-thienyl; $R_3$ and $R_4$ are both phenyl, and $R_5$ and $R_6$ are both methyl; $R_1$ and $R_2$ are both 4-cyanophenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is benzyl; $R_1$ and $R_2$ are both phenyl; $R_3$ and $R_4$ are both ethyl; $R_5$ is —H, and $R_6$ is n-butyl; $R_1$ and $R_2$ are both 2,5-dimethoxyphenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is iso-propyl; $R_1$ and $R_2$ are both 3-nitrophenyl; $R_3$ and $R_4$ are both methyl; $R_5$ is —H, and $R_6$ is methyl; $R_1$ and $R_2$ are both 4-chlorophenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is 3-thienyl; $R_1$ and $R_2$ are both phenyl; $R_3$ and $R_4$ are both methyl, and $R_5$ and $R_6$, taken together, are propylene; $R_1$ and $R_2$ are both 2,3-dimethoxyphenyl; $R_3$ and $R_4$ are both methyl; $R_5$ is —H, and $R_6$ is methyl; $R_1$ and $R_2$ are both 2-chloro-5-methoxy phenyl; $R_3$ and $R_4$ are both methyl; $R_5$ is —H, and $R_6$ is methyl; $R_1$ and $R_2$ are both 2,5-difluorophenyl; $R_3$ and $R_4$ are both methyl; $R_5$ is —H, and $R_6$ is methyl; $R_1$ and $R_2$ are both 2,5-dichlorophenyl; $R_3$ and $R_4$ are both methyl; $R_5$ is —H, and $R_6$ is methyl; $R_1$ and $R_2$ are both 2,6-dimethoxyphenyl; $R_3$ and $R_4$ are both methyl; $R_5$ is —H, and $R_6$ is methyl; $R_1$ and $R_2$ are both 2,5-dimethylphenyl; $R_3$ and $R_4$ are both methyl; $R_5$ is —H, and $R_6$ is methyl; $R_1$ and $R_2$ are both 2,5-dimethoxyphenyl; $R_3$ and $R_4$ are both ethyl; $R_5$ is —H, and $R_6$ is methyl; $R_1$ and $R_2$ are both 2,5-diethoxyphenyl; $R_3$ and $R_4$ are both methyl; $R_5$ is —H, and $R_6$ is methyl; $R_1$ and $R_2$ are both cyclopropyl; $R_3$ and $R_4$ are both methyl; $R_5$ and $R_6$ are both —H; $R_1$ and $R_2$ are both cyclopropyl; $R_3$ and $R_4$ are both ethyl; $R_5$ and $R_6$ are both —H; $R_1$ and $R_2$ are both cyclopropyl; $R_3$ and $R_4$ are both methyl; $R_5$ is methyl; $R_6$ is —H; $R_1$ and $R_2$ are both 1-methylcyclopropyl; $R_3$ and $R_4$ are both methyl; $R_5$ and $R_6$ are both —H; $R_1$ and $R_2$ are both 1-methylcyclopropyl; $R_3$ and $R_4$ are both methyl; $R_5$ is methyl and $R_6$ is —H; $R_1$ and $R_2$ are both 1-methylcyclopropyl; $R_3$ and $R_4$ are both methyl; $R_5$ is ethyl and $R_6$ is —H; $R_1$ and $R_2$ are both 1-methylcyclopropyl; $R_3$ and $R_4$ are both methyl; $R_5$ is n-propyl and $R_6$ is —H; $R_1$ and $R_2$ are both 1-methylcyclopropyl; $R_3$ and $R_4$ are both methyl; $R_5$ and $R_6$ are both methyl; $R_1$ and $R_2$ are both 1-methylcyclopropyl; $R_3$ and $R_4$ are both ethyl; $R_5$ and $R_6$ are both —H; $R_1$ and $R_2$ are both 1-methylcyclopropyl; $R_3$ is methyl, and $R_4$ is ethyl; $R_5$ and $R_6$ are both —H; $R_1$ and $R_2$ are both 2-methylcyclopropyl; $R_3$ and $R_4$ are both methyl; $R_5$ and $R_6$ are both —H; $R_1$ and $R_2$ are both 2-phenylcyclopropyl; $R_3$ and $R_4$ are both methyl; $R_5$ and $R_6$ are both —H; $R_1$ and $R_2$ are both 1-phenylcyclopropyl; $R_3$ and $R_4$ are both methyl; $R_5$ and $R_6$ are both —H; $R_1$ and $R_2$ are both cyclobutyl; $R_3$ and $R_4$ are both methyl; $R_5$ and $R_6$ are both —H; $R_1$ and $R_2$ are both cyclopentyl; $R_3$ and $R_4$ are both methyl; $R_5$ and $R_6$ are both —H; $R_1$ and $R_2$ are both cyclohexyl; $R_3$ and $R_4$ are both methyl; $R_5$ and $R_6$ are both —H; $R_1$ and $R_2$ are both cyclohexyl; $R_3$ and $R_4$ are both phenyl; $R_5$ and $R_6$ are both —H; $R_1$ and $R_2$ are both methyl; $R_3$ and $R_4$ are both methyl; $R_5$ and $R_6$ are both —H; $R_1$ and $R_2$ are both methyl; $R_3$ and $R_4$ are both t-butyl; $R_5$ and $R_6$ are both —H; $R_1$ and $R_2$ are both methyl; $R_3$ and $R_4$ are both phenyl; $R_5$ and $R_6$ are both —H; $R_1$ and $R_2$ are both t-butyl; $R_3$ and $R_4$ are both methyl; $R_5$ and $R_6$ are both —H; $R_1$ and $R_2$ are ethyl; $R_3$ and $R_4$ are both methyl; $R_5$ and $R_6$ are both —H; $R_1$ and $R_2$ are both n-propyl; $R_3$ and $R_4$ are both methyl; $R_5$ and $R_6$ are both —H. In these examples, the pharmaceutically acceptable cation represented by $M^+$ and $M^{2+}$ is as described for Structural Formula (IA), preferably $Li^+$, $Na^+$, $K^+$, $NH_3(C_2H_5OH)^+$ or $N(CH_3)_3(C_2H_5OH)^+$, more preferably $Na^+$ or $K^+$, even more preferably $Na^+$.

For many bis(thio-hydrazide amide) disalts represented by Structural Formula (IIA), Y' is —$CH_2$—. Examples include wherein: $R_1$ and $R_2$ are both phenyl, and $R_3$ and $R_4$ are both o-$CH_3$-phenyl; $R_1$ and $R_2$ are both o-$CH_3C(O)O$-phenyl, and $R_3$ and $R_4$ are phenyl; $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both phenyl, and $R_3$ and $R_4$ are both n-propyl; $R_1$ and $R_2$ are both p-cyanophenyl, and $R_3$ and $R_4$ are both methyl; $R_1$ and $R_2$ are both p-nitro phenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both n-butyl; $R_1$ and $R_2$ are both p-chlorophenyl, and $R_3$ and $R_4$ are both methyl; $R_1$ and $R_2$ are both 3-nitrophenyl, and $R_3$ and $R_4$ are both methyl; $R_1$ and $R_2$ are both 3-cyanophenyl, and $R_3$ and $R_4$ are both methyl; $R_1$ and $R_2$ are both 3-fluorophenyl, and $R_3$ and $R_4$ are both methyl; $R_1$ and $R_2$ are both 2-furanyl, and $R_3$ and $R_4$ are both phenyl; $R_1$ and $R_2$ are both 2-methoxyphenyl, and $R_3$ and $R_4$ are both methyl; $R_1$ and $R_2$ are both 3-methoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2-methoxy-5-chlorophenyl, and $R_3$ and $R_4$ are both ethyl; $R_1$ and $R_2$ are both 2,5-difluorophenyl, and $R_3$ and $R_4$ are both methyl; $R_1$ and $R_2$ are both 2,5-dichlorophenyl, and $R_3$ and $R_4$ are both methyl; $R_1$ and $R_2$ are both 2,5-dimethylphenyl, and $R_3$ and $R_4$ are both methyl; $R_1$ and $R_2$ are both 2-methoxy-5-chlorophenyl, and $R_3$ and $R_4$ are both methyl; $R_1$ and $R_2$ are both 3,6-dimethoxyphenyl, and $R_3$ and $R_4$ are both methyl; $R_1$ and $R_2$ are both phenyl, and $R_3$ and $R_4$ are both 2-ethylphenyl; $R_1$ and $R_2$ are both 2-methyl-5-pyridyl, and $R_3$ and $R_4$ are both methyl; or $R_1$ is phenyl; $R_2$ is 2,5-dimethoxyphenyl, and $R_3$ and $R_4$ are both methyl; $R_1$ and $R_2$ are both methyl, and $R_3$ and $R_4$ are both p-CF$_3$-phenyl; $R_1$ and $R_2$ are both methyl, and $R_3$ and $R_4$ are both o-CH$_3$-phenyl; $R_1$ and $R_2$ are both —CH$_2$)$_3$COOH; and $R_3$ and $R_4$ are both phenyl; $R_1$ and $R_2$ are both represented by the following structural formula:

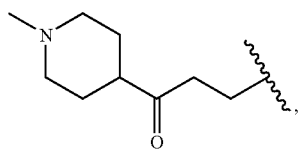 [SMILES: *CCC(=O)C1CCN(C)CC1]

and $R_3$ and $R_4$ are both phenyl; $R_1$ and $R_2$ are both n-butyl, and $R_3$ and $R_4$ are both phenyl; $R_1$ and $R_2$ are both n-pentyl, $R_3$ and $R_4$ are both phenyl; $R_1$ and $R_2$ are both methyl, and $R_3$ and $R_4$ are both 2-pyridyl; $R_1$ and $R_2$ are both cyclohexyl, and $R_3$ and $R_4$ are both phenyl; $R_1$ and $R_2$ are both methyl, and $R_3$ and $R_4$ are both 2-ethylphenyl; $R_1$ and $R_2$ are both methyl, and $R_3$ and $R_4$ are both 2,6-dichlorophenyl; $R_1$-$R_4$ are all methyl; $R_1$ and $R_2$ are both methyl, and $R_3$ and $R_4$ are both t-butyl; $R_1$ and $R_2$ are both ethyl, and $R_3$ and $R_4$ are both methyl; $R_1$ and $R_2$ are both t-butyl, and $R_3$ and $R_4$ are both methyl; $R_1$ and $R_2$ are both cyclopropyl, and $R_3$ and $R_4$ are both methyl; $R_1$ and $R_2$ are both cyclopropyl, and $R_3$ and $R_4$ are both ethyl; $R_1$ and $R_2$ are both 1-methylcyclopropyl, and $R_3$ and $R_4$ are both methyl; $R_1$ and $R_2$ are both 2-methylcyclopropyl, and $R_3$ and $R_4$ are both methyl; $R_1$ and $R_2$ are both 1-phenylcyclopropyl, and $R_3$ and $R_4$ are both methyl; $R_1$ and $R_2$ are both 2-phenylcyclopropyl, and $R_3$ and $R_4$ are both methyl; $R_1$ and $R_2$ are both cyclobutyl, and $R_3$ and $R_4$ are both methyl; $R_1$ and $R_2$ are both cyclopentyl, and $R_3$ and $R_4$ are both methyl; $R_1$ is cyclopropyl, $R_2$ is phenyl, and $R_3$ and $R_4$ are both methyl. In these examples, the pharmaceutically acceptable cation represented by M$^+$ and M$^{2+}$ is as described for Structural Formula (IA), preferably Li$^+$, Na$^+$, K$^+$, NH$_3$(C$_2$H$_5$OH)$^+$ or N(CH$_3$)$_3$(C$_2$H$_5$OH)$^+$, more preferably Na$^+$ or K$^+$, even more preferably Na$^+$.

One example of a bis(thio-hydrazide amide) disalt of the invention is:

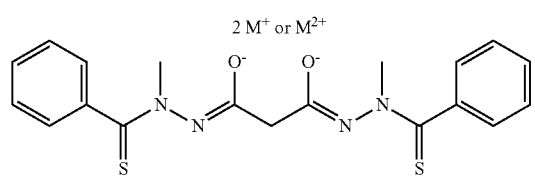

(IIIA)

wherein M$^+$ is as described for Structural Formula (IA) above.

Preferred examples of bis(thio-hydrazide amide) disalts of the present invention are the following:

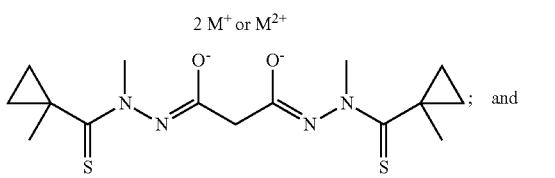

(IVA)

; and

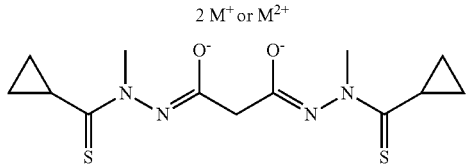

(VA)

wherein 2 M$^+$ and M$^{2+}$ are as described above for Structural Formula (IA). Preferably, the pharmaceutically acceptable cation is 2 M$^+$, wherein M$^+$ is Li$^+$, Na$^+$, K$^+$, NH$_3$(C$_2$H$_5$OH)$^+$ or N(CH$_3$)$_3$(C$_2$H$_5$OH)$^+$. More preferably, M$^+$ is Na$^+$ or K. Even more preferably, M$^+$ is Na$^+$.

In Structural Formulas (IA)-(IIA), $R_1$ and $R_2$ are the same or different and/or $R_3$ and $R_4$ are the same or different. Preferably, $R_1$ and $R_2$ are the same and $R_3$ and $R_4$ are the same.

The disclosed bis(thio-hydrazide amide) disalts may have tautomeric forms. By way of example, tautomeric forms of the compounds represented by, for example, Structural Formula (IIA) wherein Y is —CH$_2$— are shown below:

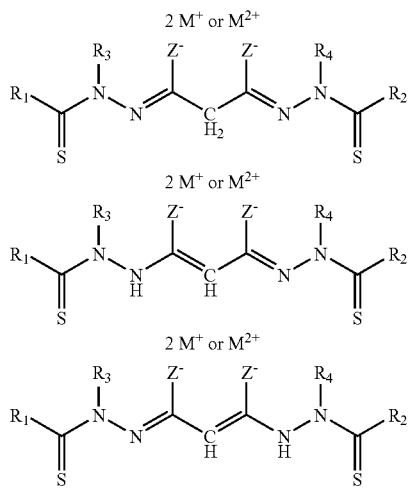

One example of a compound of the invention is Compound (19).

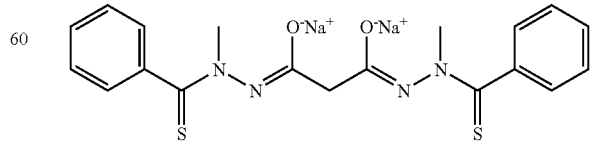

Other examples of compounds of the invention include Compounds (20)-(26).

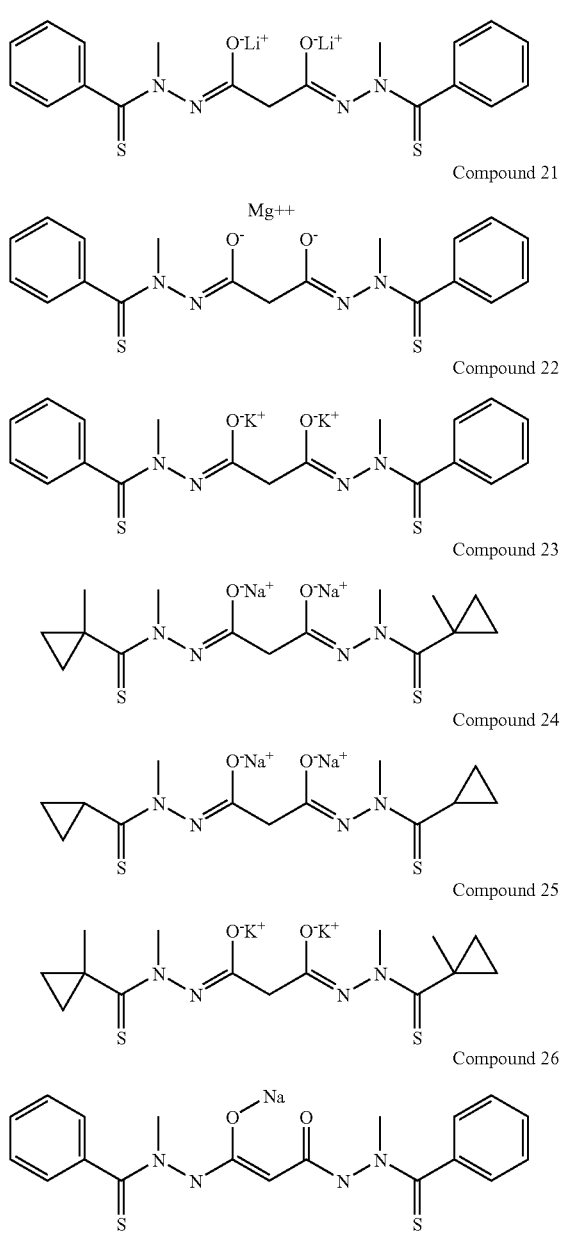

Compound 20

Compound 21

Compound 22

Compound 23

Compound 24

Compound 25

Compound 26

It is to be understood when one tautomeric form of a disclosed compound is depicted structurally, other tautomeric forms are also encompassed.

As used herein, the term "bis(thio-hydrazide amide)" and references to the Structural Formulas of this invention also include pharmaceutically acceptable salts and solvates of these compounds and Structural Formulas. Examples of acceptable salts and solvates are described in U.S. Pat. No. 7,385,084 and U.S. patent application Ser. No. 11/432,307 filed 11 May 2006, titled Synthesis Of Bis(Thio-Hydrazide Amide) Salts, the entire contents of each of which are incorporated herein by reference.

Certain compounds of the invention may be obtained as different stereoisomers (e.g., diastereomers and enantiomers). The invention includes all isomeric forms and racemic mixtures of the disclosed compounds and methods of treating a subject with both pure isomers and mixtures thereof, including racemic mixtures. Stereoisomers can be separated and isolated using any suitable method, such as chromatography.

An "alkyl group" is saturated straight or branched chain linear or cyclic hydrocarbon group. Typically, a straight chained or branched alkyl group has from 1 to about 20 carbon atoms, preferably from 1 to about 10, and a cyclic alkyl group has from 3 to about 10 carbon atoms, preferably from 3 to about 8. An alkyl group is preferably a straight chained or branched alkyl group, e.g, methyl, ethyl, n-propyl, iso-propyl, n-butyl, sec-butyl, tert-butyl, pentyl, hexyl, pentyl or octyl, or a cycloalkyl group with 3 to about 8 carbon atoms. A $C_1$-$C_8$ straight chained or branched alkyl group or a $C_3$-$C_8$ cyclic alkyl group is also referred to as a "lower alkyl" group. Suitable substituents for an alkyl group are those which do not substantially interfere with the anti-cancer activity of the disclosed compounds. Preferred substituents on alkyl groups include, —OH, —NH$_2$, —NO$_2$, —CN, —COON, halogen, aryl, $C_1$-$C_8$ alkoxy, $C_1$-$C_8$ haloalkoxy and —CO($C_1$-$C_8$ alkyl). More preferred substituents on alkyl groups include —OH, halogen, phenyl, benzyl, pyridyl, and $C_1$-$C_8$ alkoxy. More preferred substituents on alkyl groups include —OH, halogen, and $C_1$-$C_4$ alkoxy.

A "straight chained hydrocarbyl group" is an alkylene group, i.e., —(CH$_2$)$_y$—, with one or more (preferably one) internal methylene groups optionally replaced with a linkage group. The variable "y" is a positive integer (e.g., between 1 and 10), preferably between 1 and 6 and more preferably 1 or 2. A "linkage group" refers to a functional group which replaces a methylene in a straight chained hydrocarbyl. Examples of suitable linkage groups include a carbonyl (—C(O)—), alkene, alkyne, phenylene, ether (—O—), thioether (—S—), or amine (—N($R^a$)—), wherein $R^a$ is defined below. A preferred linkage group is —C($R_5R_6$)—, wherein $R_5$ and $R_6$ are defined above. Suitable substituents for an alkylene group and a hydrocarbyl group are those which do not substantially interfere with the anti-cancer activity of the disclosed compounds. $R_5$ and $R_6$ are preferred substituents for an alkylene or hydrocarbyl group represented by Y.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g, methyl, ethyl, n-propyl, iso-propyl, n-butyl, sec-butyl, tert-butyl, pentyl, hexyl, pentyl or octyl, or a cycloalkyl group with 3 to about 8 carbon atoms. A $C_1$-$C_8$ straight chained or branched alkyl group or a $C_3$-$C_8$ cyclic alkyl group is also referred to as a "lower alkyl" group.

The term "aromatic group" may be used interchangeably with "aryl," "aryl ring," "aromatic ring," "aryl group" and "aromatic group." Aromatic groups include carbocyclic aromatic groups such as phenyl, naphthyl, and anthracyl, and heteroaryl groups such as imidazolyl, thienyl, furanyl, pyridyl, pyrimidy, pyranyl, pyrazolyl, pyrroyl, pyrazinyl, thiazole, oxazolyl, and tetrazole. The term "heteroaryl group" may be used interchangeably with "heteroaryl," "heteroaryl ring," "heteroaromatic ring" and "heteroaromatic group." Heteroaryl groups are aromatic groups that comprise one or more heteroatom, such as sulfur, oxygen and nitrogen, in the ring structure. Preferably, heteroaryl groups comprise from one to four heteroatoms. Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

Non-aromatic heterocyclic rings are non-aromatic rings which include one or more heteroatoms such as nitrogen, oxygen or sulfur in the ring. The ring can be five, six, seven or eight-membered. Preferably, heterocyclic groups comprise from one to about four heteroatoms. Examples include tetrahydrofuranyl, tetrahyrothiophenyl, morpholino, thiomorpholino, pyrrolidinyl, piperazinyl, piperidinyl, and thiazolidinyl.

Suitable substituents on an alkyl, aliphatic group (including an alkylene group), non-aromatic heterocyclic group, benzylic or aryl group (carbocyclic and heteroaryl) are those which do not substantially interfere with the anti-cancer activity of the disclosed compounds. A substituent substantially interferes with anti-cancer activity when the anti-cancer activity is reduced by more than about 50% in a compound with the substituent compared with a compound without the substituent. Examples of suitable substituents include —$R^a$, —OH, —Br, —Cl, —I, —F, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NR^cCOR^a$, —$NHCONH_2$, —$NHCONR^aH$, —$NHCON(R^aR^b)$, —$NR^cCONH_2$, —$NR^c$-$CONR^aH$, —$NR^cCON(R^aR^b)$, —$C(=NH)$—$NH_2$, —$C(=NH)$—$NHR^a$, —$C(=NH)$—$N(R^aR^b)$, —$C(=NR^c)$—$NH_2$, —$C(=NR^c)$—$NHR^a$, —$C(=NR^c)$—$N(R^aR^b)$, —NH—$C(=NH)$—$NH_2$, —NH—$C(=NH)$—$NHR^a$, —NH—$C(=NH)$—$N(R^aR^b)$, —NH—$C(=NR^c)$—$NH_2$, —NH—$C(=NR^c)$—$NHR^a$, —NH—$C(=NR^c)$—$N(R^aR^b)$, —$NR^dH$—$C(=NH)$—$NH_2$, —$NR^d$—$C(=NH)$—$NHR^a$, —$NR^d$—$C(=NH)$—$N(R^aR^b)$, —$NR^d$—$C(=NR^c)$—$NH_2$, —$NR^d$—$C(=NR^c)$—$NHR^a$, —$NR^d$—$C(=NR^c)$—$N(R^aR^b)$, —$NHNH_2$, —$NHNHR^a$, —$NHR^aR^b$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —S(O)$R^a$, and —S(O)$_2R^a$.

$R^a$-$R^d$ are each independently an alkyl group, aromatic group, non-aromatic heterocyclic group or —$N(R^aR^b)$, taken together, form a non-aromatic heterocyclic group. The alkyl, aromatic and non-aromatic heterocyclic group represented by $R^a$—$R^d$ and the non-aromatic heterocyclic group represented by —$N(R^aR^b)$ are each optionally and independently substituted with one or more groups represented by $R^\#$. Preferably $R^a$-$R^d$ are unsubstituted.

$R^\#$ is $R^+$, —$OR^+$, —O(haloalkyl), —$SR^+$, —$NO_2$, —CN, —NCS, —$N(R^+)_2$, —$NHCO_2R^+$, —$NHC(O)R^+$, —NHNHC(O)$R^+$, —$NHC(O)N(R^+)_2$, —$NHNHC(O)N(R^+)_2$, —$NHNHCO_2R^+$, —$C(O)C(O)R^+$, —$C(O)CH_2C(O)R^+$, —$CO_2R^+$, —$C(O)R^+$, —$C(O)N(R^+)_2$, —$OC(O)R^+$, —$OC(O)N(R^+)_2$, —$S(O)_2R^+$, —$SO_2N(R^+)_2$, —$S(O)R^+$, —$NHSO_2N(R^+)_2$, —$NHSO_2R^+$, —$C(=S)N(R^+)_2$, or —$C(=NH)$—$N(R^+)_2$.

$R^+$ is —H, a $C_1$-$C_4$ alkyl group, a monocyclic heteroaryl group, a non-aromatic heterocyclic group or a phenyl group optionally substituted with alkyl, haloalkyl, alkoxy, haloalkoxy, halo, —CN, —$NO_2$, amine, alkylamine or dialkylamine. Preferably $R^+$ is unsubstituted. Optionally, the group —$N(R^+)_2$ is a non-aromatic heterocyclic group, provided that non-aromatic heterocyclic groups represented by $R^+$ and —$N(R^+)_2$ that comprise a secondary ring amine are optionally acylated or alkylated.

Preferred substituents for a phenyl group, including phenyl groups represented by $R_1$-$R_4$, include $C_1$-$C_4$ alkyl, $C_1$-$C_4$ alkoxy, $C_1$-$C_4$ haloalkyl, $C_1$-$C_4$ haloalkoxy, phenyl, benzyl, pyridyl, —OH, —$NH_2$, —F, —Br, —I, —$NO_2$ or —CN. More preferred for a phenyl group, including phenyl groups represented by $R_1$-$R_4$, include $R_1$ and $R_2$ are optionally substituted with —OH, —CN, halogen, $C_{1-4}$ alkyl or $C_1$-$C_4$ alkoxy.

Preferred substituents for a cycloalkyl group, including cycloalkyl groups represented by $R_1$ and $R_2$, are alkyl groups, such as a methyl or ethyl group.

As used herein, the term "GRAS" refers to any substance which is categorized by the USFDA as GRAS ("Generally Recognized As Safe"). Components meriting such a designation are found in Title 21 of the US Code of Federal Regulations, the contents of which are incorporated herein by reference. In one aspect of the invention the GRAS excipient is TPGS/PEG400. In one aspect of the invention the GRAS excipient is 20% TPGS/80% PEG400.

As used herein, the term "phospholipid" refers to a triester of glycerol with two fatty acids and one phosphate ion. Exemplary phospholipids useful in the present invention include, but are not limited to, phosphatidyl chlorine, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. The phospholipids can have any combination of fatty acid as its fatty acyl side chain, for example, the phospholipids can have a saturated fatty acid such as a decanoic acid, lauric acid, myristic acid, palmitic acid, stearic acid, icosanoic acid, (a $C_{20}$ saturated fatty acid); sodium behenic acid, or an unsaturated fatty acid such as myristoleic acid, palmitoleic acid, oleic acid, sodium linoleic acid, alpha linolenic acid, sodium arachidonic acid, eicosapentanoic acid, and the like. The two fatty acyl residues on the phospholipids may be the same or they may be different fatty acids. The phospholipid component of the drug delivery composition can be either a single phospholipid or a mixture of several phospholipids.

In one aspect, the phospholipids used as emulsifiers in the present invention are naturally occurring phospholipids from a natural origin. For example, naturally occurring lecithin is a mixture of the diglycerides of stearic, palmitic, and oleic acids, linked to the choline ester of phosphoric acid, commonly called phosphatidylcholine, and can be obtained from a variety of sources such as eggs and soya beans. Soy lecithin and egg lecithin (including hydrogenated versions of these compounds) have been characterized in various compositions and are generally recognized to be safe, have combined emulsification and solubilization properties, and tend to be broken down into innocuous substances more rapidly than most synthetic surfactants. Commercially available soya phospholipids include the CENTROPHASE and CENTROLEX products marketed and sold by Central Soya, PHOSPHOLIPON from Phospholipid GmbH, Germany, LIPOID by Lipoid GmbH, Germany, and EPIKURON by Degussa.

Synthetic phospholipids, diacylglycerols and triacylglyercols also may be used as emulsifiers herein. For example, common synthetic lipids known to be useful as typical emulsifiers include, but are not limited to diacylglycerols such as 1,2-Dilauroyl-sn-glycerol (DLG), 1,2-Dimyristoyl-sn-glycerol (DMG), 1,2-Dipalmitoyl-sn-glycerol (DPG), 1,2-Distearoyl-sn-glycerol (DSG); phosphatidic acids such as 1,2-Dimyristoyl-sn-glycero-3-phosphatidic acid, sodium salt (DMPA,Na), 1,2-Dipalmitoyl-sn-glycero-3-phosphatidic acid, sodium salt (DPPA,Na), 1,2-Distearoyl-sn-glycero-3-phosphatidic acid, sodium salt-(DSPA,Na); phosphatidylcholines such as 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine
(DPPC), 1,2-Dipalmitoyl-sn-glycero-3-phosphocholine
(DPPC), 1,2-Distearoyl-sn-glycero-3-phosphocholine
(DSPC), 1,2-Distearoyl-sn-glycero-3-phosphocholine
(DSPC); phosphatidylethanolamines such as 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Distearoyl-sn-glycero-3-phosphoethanolamine (DSPE); phosphatidylclyerols such as 1,2-Dilauroyl-sn-glycero-3-phosphoglycerol, sodium salt (DLPG), 1,2-Dimyristoyl-sn-glycero-3-phosphoglycerol, sodium salt (DMPG), 1,2-Dimyristoyl-sn-glycero-3-phospho-sn-1-glycerol, ammonium salt (DMP-sn-1-G,NH4), 1,2-Dipalmitoyl-sn-glycero-3-phosphoglycerol, sodium salt (DPPG,Na), 1,2-Distearoyl-sn-glycero-3-phosphoglycerol, sodium salt (DSPG,Na), 1,2-Distearoyl-sn-glycero-3-phospho-sn-1-glycerol, sodium salt (DSP-sn-1G,Na), phosphatidylserines such as 1,2-Dipalmitoyl-sn-glycero-3-phospho-L-serine, sodium salt (DPPS,Na). The emulsifier composition can be made up of mixtures of the aforementioned phospholipids as well as phosphatidylinositols, cardiolipins. In addition, it is contemplated that mixed chain phospholipids also will be useful synthetic phospholipids emulsifiers for use herein. Such mixed chain phospholipids include, for example, 1-Palmitoyl-2-oleoyl-sn-glycero-3-phosphocholine (POPC), 1-Palmitoyl-2-oleoyl-sn-glycero-3-phosphoglycerol, sodium salt (POPG,Na), 1-Palmitoyl-2-oleoyl-sn-glycero-3-phosphoglycerol, ammonium salt (POPG,NH4). Additionally, lysophospholipids (i.e., phospholipids in which one of the two fatty acyl residues of the phospholipids is absent) may be useful emulsifiers. Exemplary lysophospholipids include 1-Palmitoyl-2-lyso-sn-glycero-3-phosphocholine (P-lyso-PC) and 1-Stearoyl-2-lyso-sn-glycero-3-phosphocholine (S-lyso-PC). One or more of the phospholipids also may be PEGylated.

As used herein, the term "cyclodextrin" refers to a cyclic oligosaccharide consisting of at least five saccharide units (e.g., glucopyranose units). For example, the term "cyclodextrin" includes a cyclic molecule containing six or more α-D-glucopyranose units linked at the 1,4 positions by a linkages, as in amylose, as well as a cyclic molecule containing seven α-D-glucopyranose units, as in cycloheptaamylose. The term "cyclodextrin" also includes any of the known cyclodextrins, such as unsubstituted cyclodextrins containing from six to twelve glucose units. Thus, the term "cyclodextrin" includes at least beta-cyclodextrin (β-CD or BCD), which is commercially available (e.g., product no. C-4805 from Sigma-Aldrich Corp., St. Louis, Mo., USA, cell culture grade β-CD (Schardinger β-Dextrin; Cycloheptaamylose)), as well as alpha-cyclodextrin (α-CD or ACD) and γ-cyclodextrin (γ-CD or GCD) and/or their derivatives and/or mixtures thereof. The α-cyclodextrin consists of six glucose units, the β-cyclodextrin consists of seven glucose units, and the γ-cyclodextrin consists of eight glucose units arranged in donut-shaped rings.

The term "derivative of cyclodextrin" is meant to include a cyclodextrin molecule wherein some of the OH groups are converted to OR groups. For example, cyclodextrin derivatives include those substituted with lower alkyl groups such as methylated cyclodextrins and ethylated cyclodextrins, wherein R is a methyl or an ethyl group. Lower alkyls contain from 1 to 6 carbon atoms and may be straight chain or branched. In addition, cyclodextrin derivatives include those with hydroxyalkyl substituted groups, such as hydroxypropyl cyclodextrins and/or hydroxyethyl cyclodextrins, wherein R is a —CH$_2$, —CH(OH)$_2$—CH$_3$ or a —CH$_2$CH$_2$—OH group. Substitution may occur at some or all of the hydroxyl groups. By way of example, a derivative of β-cyclodextrin is methyl-β-cyclodextrin (MBCD). The term "methyl-β-cyclodextrin" refers to a β-cyclodextrin having hydroxyl sites substituted by methoxy groups to varying degrees. For example, MBCD can be totally saturated, i.e., 80-100% substituted. Alternatively, the mean degree of substitution can be about 1.5-2.1 methyl units/glucose, i.e., approximately 25-33% substituted. Methyl-β-cyclodextrin useful in the invention is commercially available (e.g., product no. C-4555, Sigma).

"Derivative of cyclodextrin" also include cyclodextrin derivatives such as hydroxypropyl and sulfobutyl ether cyclodextrins and others. Such derivatives are described for example, in U.S. Pat. Nos. 4,727,064 and 5,376,645. Hydroxypropylated β-cyclodextrins (HPBCD) are commercially available (e.g., 2-hydropropyl-(3-cyclodextrin, product no. C-0926, Sigma); as are Hydroxypropylated α-cyclodextrins (HPACD) (e.g., CAVASOL® W6 HP, Wacker Biochem Corp. USA, Eddyville, Iowa 52553) and hydroxypropylated γ-cyclodextrins (HPGCD) (e.g., CAVASOL® W8 HP, Wacker Biochem Corp.). Sulfobutyl-ether-β-cyclodextrin are also commercially available. Additional cyclodextrin derivatives are disclosed, for example, in U.S. Pat. No. 6,001,343.

In one aspect, the cyclodextrin is selected from the group consisting of 2,6-dimethyl-β-cyclodextrin, 2-hydroxyethyl-β-cyclodextrin, 2-hydroxypropyl-β-cyclodextrin, 2-hydroxyethyl-γ-cyclodextrin, 2-hydroxypropyl-γ-cyclodextrin, (2-carboxymethoxy)propyl-β-cyclodextrin, and sulfobutylether-7-β-cyclodextrin. In one aspect, the cyclodextrin is 2-hydroxypropyl-β-cyclodextrin.

Aqueous pharmaceutical suspension compositions typically contain one or more polymeric suspending or viscosity-enhancing agents to enhance physical stability. The polymeric suspending agents, which can be ionic or nonionic, help keep the water-insoluble components of the composition suspended. The polymeric suspending agents also make it easier to resuspend the composition after water-insoluble components have settled to the bottom of a container.

Many polymeric suspending agents are known in the art. Examples of polymeric suspending agents commonly used in aqueous pharmaceutical suspension compositions include but include but are not limited to carbomers, polyvinyl alcohol, polyvinyl pyrrolidone, hydroxypropylmethyl cellulose, hydroxyethyl cellulose, hydroxypropyl cellulose, methyl cellulose, carboxymethyl cellulose, microcrystalline cellulose, powdered cellulose, xanthan gum, gellan gum, carageenan, acacia, tragacanth, gelatin, guar gum, alginic acid, sodium alginates, propylene glycol alginate, eudragit (methacrylic acid and methyl methacrylate copolymer), dextrin, dextran, dextran-polyethylene glycol conjugates, and the glycosaminoglycans family of polymers, such as heparin sulfate, heparan sulfate, dermatan sulfate, chondroitin sulfate.

One aspect of the invention is a nanoparticle (nanoparticulate) formulation of compounds of the invention. Preparing nanoparticle formulations generally comprises one of the following methods: milling, precipitation, homogenization, evaporation, supercritical fluids, or a combination thereof. Exemplary methods of making nanoparticulate active agent compositions are described in U.S. Pat. No. 5,145,684. Methods of making nanoparticulate active agent compositions are also described in U.S. Pat. Nos. 5,518,187; 5,718,388; 5,862,999; 5,665,331; 5,662,883; 5,560,932; 5,543,133; 5,534,270; 5,510,118; and 5,470,583, all of which are specifically incorporated by reference.

As used herein, "Hsp70" includes each member of the family of heat shock proteins having a mass of about 70-kiloDaltons, including forms such as constituitive, cognate, cell-specific, glucose-regulated, inducible, etc. Examples of specific Hsp70 proteins include hsp70, hsp70hom; hsc70; Grp78/BiP; mt-hsp70/Grp75, and the like). Typically, the disclosed methods increase expression of inducible Hsp70. Functionally, the 70-kDa HSP (HSP70) family is a group of chaperones that assist in the folding, transport, and assembly of proteins in the cytoplasm, mitochondria, and endoplasmic reticulum. Membrane-bound Hsp70 In humans, the Hsp70 family encompasses at least 11 genes encoding a group of highly related proteins. See, for example, Tavaria, et al., *Cell Stress Chaperones*, 1996, 1(1):23-28; Todryk, et al., Immunology, 2003, 110(1): 1-9; and Georgopoulos & Welch, *Annu. Rev. Cell Biol.*, 1993, 9:601-634; the entire teachings of these documents are incorporated herein by reference.

As used herein, an "Hsp70-responsive disorder" is a medical condition wherein stressed cells can be treated by increased Hsp70 expression. Such disorders can be caused by a wide variety of cellular stressors, including, but not limited to Alzheimers' disease; Huntington's disease; Parkinson's disease; spinal/bulbar muscular atrophy (e.g., Kennedy's disease), spinocerebellar ataxic disorders, and other neuromuscular atrophies; familial amyotrophic lateral sclerosis; ischemia; seizure; hypothermia; hyperthermia; burn trauma; atherosclerosis; radiation exposure; glaucoma; toxin exposure; mechanical injury; inflammation; autoimmune disease; infection (bacterial, viral, fungal, or parasitic); and the like.

In some embodiments, the Hsp70-responsive disorder is a neurodegenerative disorder. As used herein, a neurodegenerative disorder involves degradation of neurons such as cereberal, spinal, and peripheral neurons (e.g., at neuromuscular junctions), more typically degradation of cerebral and spinal neurons, or in preferred embodiments, degradation of cerebral neurons. Neurodegenerative disorders can include Alzheimers' disease; Huntington's disease; Parkinson's disease; spinal/bulbar muscular atrophy and other neuromuscular atrophies; and familial amyotrophic lateral sclerosis or other diseases associated with superoxide dismutase (SOD) mutations. Neurodegenerative disorders can also include degradation of neurons caused by ischemia, seizure, thermal stress, radiation, toxin exposure, infection, injury, and the like.

In some embodiments, the Hsp70-responsive disorder is a disorder of protein aggregation/misfolding, such as Alzheimers' disease; Huntington's disease; Parkinson's disease; spongiform encephalopathies; and the like.

In another embodiment the Hsp70 responsive disorder is a treatment or condition which causes or may cause nerve damage. The compounds for use in the methods of the present invention can be used to reduce or prevent (inhibit the onset of) nerve damage (i.e., provide neuroprotection) in a subject i) suffering from a condition which causes or may cause nerve damage or ii) receiving treatment which causes or may cause nerve damage. In one aspect, the treatment which causes or may cause nerve damage is radiation therapy. In another aspect, the treatment is chemotherapy. In one aspect, the chemotherapy comprises administering an antimitotic agent (e.g. vincristine, vinorelbine, paclitaxel, or a paclitaxel analog). In one aspect, the chemotherapy comprises administering paclitaxel. In another aspect, the chemotherapy comprises administering a platinum derivative (e.g. cisplatinum, carboplatin, or oxaliplatin). In certain embodiments, the compounds for use in the methods of the present invention can be administered simultaneously as a combination therapy with the treatment which causes or may cause nerve damage. In other embodiments the compounds for use in the methods of the present invention can be administered before or after the treatment which causes may cause nerve damage. In certain embodiments the compounds for use in the methods of the present invention can be administered between 30 minutes and 12 hours, between 1 hour and 6 before or after the treatment which causes or may cause nerve damage.

Nerve damage may be caused by a number of treatments including, but not limited to, radiation therapy; chemotherapy, e.g. cisplatinum, carboplatin, oxaliplatin, vincristine, vinblastine, vinorelbine, vindesine, ifosfamide, methotrexate, cladribine, altretamine, fludarabine, procarbazine, thiotepa, teniposide, arsenic trioxide, alemtuzumab, capecitabine, dacarbazine, denileukin diftitox, interferon alpha, liposomal daunorubicin, tretinoin, etoposide/VP-16, cytarabine, hexamethylmelamine, suramin, paclitaxel, docetaxel, gemcitibine, thalidomide, and bortezomib; heart or blood pressure medications, e.g. amiodarone, hydralazine, digoxin, and perhxiline; medications to fight infection, e.g. metronidazole, nitrofurantoin, thalidomide, and INH; medications to treat skin conditions, e.g. dapsone; anticonvulsants, e.g. phenyloin; anti-alcohol medications, e.g. disulfuram; HIV medications, e.g. zidovudine, didanonsine, stavudine, zalcitabine, ritonavir, d4T, ddC, ddI, and amprenavir; cholesterol medications, e.g. lovastatin, pravastatin, indapamid, simvastatin, fluvastatin, atorvastatin, cerivastatin, and gemfibrozil; anti-rheumatics, e.g. chloroquine, cholchicine, organic gold, and penicillamine; nitrous oxide; lithium; and ergots.

In some embodiments, the Hsp70-responsive disorder is ischemia. Ischemia can damage tissue through multiple routes, including oxygen depletion, glucose depletion, oxidative stress upon reperfusion, and/or glutamate toxicity, and the like. Ischemia can result from an endogenous condition (e.g., stroke, heart attack, and the like), from accidental mechanical injury, from surgical injury (e.g., reperfusion stress on transplanted organs), and the like. Alternatively, tissues that can be damaged by ischemia include neurons, cardiac muscle, liver tissue, skeletal muscle, kidney tissue, pulmonary tissue, pancreatic tissue, and the like. In one preferred embodiment, the Hsp70-responsive disorder is cerebral or spinal ischemia. In another preferred embodiment, the Hsp70-responsive disorder is cardiac ischemia.

In various embodiments, the Hsp70-responsive disorder is seizure, e.g., eplileptic seizure, injury-induced seizure, chemically-induced seizure, and the like.

In some embodiments, the Hsp70-responsive disorder is due to thermal stress. Thermal stress includes hyperthermia (e.g., from fever, heat stroke, burns, and the like) and hypothermia. In a preferred embodiment the disorder is hyperthermia. In another preferred embodiment, the Hsp70-responsive disorder is burn trauma.

In preferred embodiments, the Hsp70-responsive disorder is atherosclerosis.

In various embodiments, the Hsp70-responsive disorder is radiation damage, e.g., due to visible light, ultraviolet light, microwaves, cosmic rays, alpha radiation, beta radiation, gamma radiation, X-rays, and the like. For example, the damage could be radiation damage to non-cancerous tissue in a subject treated for cancer by radiation therapy. In a preferred embodiment, the Hsp70-responsive disorder is radiation damage from visible light or ultraviolet light.

In various embodiments, the Hsp70-responsive disorder is mechanical injury, e.g., trauma from surgery, accidents, certain disease conditions (e.g., pressure damage in glaucoma) and the like. In a preferred embodiment, the Hsp70-responsive disorder is cerebral or spinal trauma. In another preferred embodiment, the Hsp70-responsive disorder is glaucoma (leading to pressure damage to retinal ganglions).

In various embodiments, the Hsp70-responsive disorder is exposure to a toxin. In preferred embodiments, the Hsp70- responsive disorder is exposure to a neurotoxin selected from methamphetamine; antiretroviral HIV therapeutics (e.g., nucleoside reverse transcriptase inhibitors; heavy metals (e.g., mercury, lead, arsenic, cadmium, compounds thereof, and the like), amino acid analogs, chemical oxidants, ethanol, glutamate, metabolic inhibitors, antibiotics, and the like.

Certain compounds of the invention also increase Natural Killer (NK) cell activity. As used herein, a "NK cell-responsive disorder" is a medical condition which is improved by an increased in NK cell activity. For example, a subject with a NK cell-responsive disorder may need immune system augmentation because of infection or the possibility thereof. In some embodiments, such a subject can have an infection (or has been exposed to an infectious environment where pathogens are present, e.g., in a hospital) the symptoms of which may be alleviated by the methods disclosed herein. For example, a subject in need of treatment can have an infection (bacterial, viral, fungal, or parasitical (protozoal)) for which the disclosed methods of activating NK cells can be a treatment.

In some embodiments, a subject having an NK cell-responsive disorder has an immunodeficiency. Such a subject is in need of or can benefit from prophylactic therapy, for example, a subject that has incomplete, damaged or otherwise compromised defenses against infection, or is subject to an infective environment, or the like. For example, a subject can be in an infectious environment where pathogens are present, e.g., in a hospital; can have an open wound or burn injury; can have an inherited or acquired immune deficiency (e.g., severe combined immunodeficiency or "bubble boy" syndrome, variable immunodeficiency syndrome acquired immune deficiency syndrome (AIDS), or the like); can have a depressed immune system due to physical condition, age, toxin exposure, drug effect (immunosuppressants, e.g., in a transplant recipient) or side effect (e.g., due to an anticancer agent); or the like.

In some embodiments, NK cell activity can be increased in subjects that have decreased or deficient NK cell activity, in conditions such as chronic fatigue syndrome (chronic fatigue immune dysfunction syndrome) or Epstein-Barr virus infection, post viral fatigue syndrome, post-transplantation syndrome (especially allogeneic transplants) or host-graft disease, exposure to drugs such as anticancer agents or nitric oxide synthase inhibitors, natural aging, and various immunodeficient conditions such as severe combined immunodeficiency, variable immunodeficiency syndrome, and the like.

In some embodiments, a subject having an NK cell-responsive disorder is in need of treatment for bacteremia. Bacteremia is the condition of bacterial infection in the bloodstream. Septic shock includes serious localized or bacteremic infection accompanied by systemic inflammation, in other words sepsis with hypoperfusion and hypotension refractory to fluid therapy. Sepsis, or systemic inflammatory response syndrome, includes various severe conditions such as infections, pancreatitis, burns, trauma) that can cause acute inflammation. Septic shock is typically related to infections by gram-negative organisms, staphylococci, or meningococci. Septic shock can be characterized by acute circulatory failure, typically with hypotension, and multiorgan failure.

Transient bacteremia can be caused by surgical or trauma wounds. Gram-negative bacteremia can be intermittent and opportunistic; although it may have no effect on a healthy person, it may be seriously important in immunocompromised patients with debilitating underlying diseases, after chemotherapy, and in settings of malnutrition. The infection can typically be in the lungs, in the genitouritory (GU) or gastrointestinal (GI) tract, or in soft tissues, e.g., skin in patients with decubitus ulcer, oral ulcers in patients at risk, and patients with valvular heart disease, prosthetic heart valves, or other implanted prostheses.

Typically, gram-negative bacteremia can manifest in chronically ill and immunocompromised patients. Also in such patients, bloodstream infections can be caused by aerobic bacilli, anaerobes, and fungi. Bacteroides can lead to abdominal and pelvic infective complications, especially in females. Transient or sustained bacteremia can typically result in metastatic infection of the meninges or serous cavities, such as the pericardium or larger joints. *Enterococcus, staphylococcus*, or fungus can lead to endocarditis, but is less common with gram-negative bacteremia. Staphylococcal bacteremia can be typical of IV drug users, and can be a typical cause of gram-positive bacterial endocarditis.

The incidence of systemic fungal infections has undergone a significant increase, particularly in humans, due in part to increases in the number of subjects with compromised immune systems, for example, the elderly, AIDS patients, patients undergoing chemotherapy, burn patients, patients with diabetic ketoacidosis, and transplant patients on immunosuppressive drugs. A study found that about 40% of deaths from infections acquired during hospitalization were due to mycoses. See Sternberg, et. al, *Science*, 1994, 266:1632-1634, the entire teachings of which are incorporated herein by reference.

In various embodiments, the subject having an NK cell-responsive disorder can be in need of treatment for a fungal infection, such as a pathogenic dermatophyte, a pathogenic filamentous fungus, and/or a pathogenic non-filamentous fungus, e.g., a yeast, or the like. Pathogenic dermatophytes can include, e.g., species of the genera *Trichophyton, Tinea, Microsporum, Epidermophyton*, or the like. Pathogenic filamentous fungus can include, e.g., species of genera such as *Aspergillus, Histoplasma, Cryptococcus, Microsporum*, or the like. Pathogenic non-filamentous fungus, e.g., yeasts, can include, for example, species of the genera *Candida, Malassezia, Trichosporon, Rhodotorula, Torulopsis, Blastomyces, Paracoccidioides, Coccidioides*, or the like. In various embodiments, the subject can be treated for a fungal infection from a species of the genera *Aspergillus* or *Trichophyton*. Species of *Trichophyton* can include, for example, *Trichophyton mentagrophytes, Trichophyton rubrum, Trichophyton schoenleinii, Trichophyton tonsurans, Trichophyton verrucosum*, and *Trichophyton violaceum*. Species of *Aspergillus* can include, for example, *Aspergillus fumigatus, Aspergillus flavus, Aspergillus niger, Aspergillus amstelodami, Aspergillus candidus, Aspergillus carneus, Aspergillus nidulans, A oryzae, Aspergillus restrictus, Aspergillus sydowi, Aspergillus terreus, Aspergillus ustus, Aspergillus versicolor, Aspergillus caesiellus, Aspergillus clavatus, Aspergillus avenaceus*, and *Aspergillus deflectus*. In some embodiments, the subject can be treated for a fungal infection from a pathogenic dermatophyte, e.g., *Trichophyton* (e.g., *Trichophyton rubrum*), *Tinea, Microsporum*, or *Epidermophyton*; or *Cryptococcus* (e.g., *Cryptococcus neoformans*) *Candida* (e.g., *Candida albicans*), *Paracoccidioides* (e.g., *Paracoccidioides brasiliensis*), or *Coccidioides* (e.g., *Coccidioides immitis*). In particular embodiments, the subject can be treated for a fungal infection from *Trichophyton rubrum, Cryptococcus neoformans, Candida albicans, Paracoccidioides brasiliensis*, or *Coccidioides immitis*.

Thus, in various embodiments, a subject can have an infection caused by a fungus selected from the genera *Trichophyton, Tinea, Microsporum, Epidermophyton, Aspergillus, Histoplasma, Cryptococcus, Microsporum, Candida, Malassezia, Trichosporon, Rhodotorula, Torulopsis, Blastomyces, Paracoccidioides*, and *Coccidioides*. In some embodiments, the subject can have an infection caused by a fungus selected from the genera *Trichophyton, Tinea, Microsporum, Epidermophyton; Cryptococcus, Candida, Paracoccidioides*, and *Coccidioides*. In certain embodiments, the subject can have an infection caused by a fungus selected from *Trichophyton rubrum, Cryptococcus neoformans, Candida albicans, Paracoccidioides brasiliensis,* and *Coccidioides immitis.*

In various embodiments, the subject having an NK cell-responsive disorder can be in need of treatment for a bacterial infection caused, for example, by a bacteria of a genus selected from *Allochromatium, Acinetobacter, Bacillus, Campylobacter, Chlamydia, Chlamydophila, Clostridium, Citrobacter, Escherichia, Enterobacter, Enterococcus, Francisella, Haemophilus, Helicobacter, Klebsiella, Listeria, Moraxella, Mycobacterium, Micrococcus, Neisseria, Proteus, Pseudomonas, Salmonella, Serratia, Shigella, Stenotrophomonas, Staphyloccocus, Streptococcus, Synechococcus, Vibrio,* and *Yersina;* or anaerobic bacterial genera such as *Peptostreptococci, Porphyromonas, Actinomyces, Clostridium, Bacteroides, Prevotella, Anaerobiospirillum, Fusobacterium,* and *Bilophila*. In some embodiments, the subject having an NK cell-responsive disorder can be in need of treatment for a bacterial infection from *Allochromatium vinosum, Acinetobacter baumanii, Bacillus anthracis, Campylobacter jejuni, Chlamydia trachomatis, Chlamydia pneumoniae, Clostridium* spp., *Citrobacter* spp., *Escherichia coli, Enterobacter* spp., *Enterococcus faecalis, Enterococcus faecium, Francisella tularensis, Haemophilus influenzae, Helicobacter pylori, Klebsiella* spp., *Listeria monocytogenes, Moraxella catarrhalis, Mycobacterium tuberculosis, Neisseria meningitidis, Neisseria gonorrhoeae, Proteus mirabilis, Proteus vulgaris, Pseudomonas aeruginosa, Salmonella* spp., *Serratia* spp., *Shigella* spp., *Stenotrophomonas maltophilia, Staphyloccocus aureus, Staphyloccocus epidermidis, Streptococcus pneumoniae, Streptococcus pyogenes, Streptococcus agalactiae, Yersina pestis,* and *Yersina enterocolitica,* or the like; or *Peptostreptococci asaccharolyticus, Peptostreptococci magnus, Peptostreptococci micros, Peptostreptococci prevotii, Porphyromonas asaccharolytica, Porphyromonas canoris, Porphyromonas gingivalis, Porphyromonas macaccae, Actinomyces israelii, Actinomyces odontolyticus, Clostridium innocuum, Clostridium clostridioforme, Clostridium difficile, Bacteroides tectum, Bacteroides ureolyticus, Bacteroides gracilis (Campylobacter gracilis), Prevotella intermedia, Prevotella heparinolytica, Prevotella oris-buccae, Prevotella bivia, Prevotella melaminogenica, Fusobacterium naviforme, Fusobacterium necrophorum, Fusobacterium varium, Fusobacterium ulcerans, Fusobacterium russii, Bilophila wadsworthia, Haemophilus ducreyi; Calymmatobacterium granulomatis,* or the like.

It is believed that compounds of the invention can be particularly useful for treating a subject with an intracellular infection. It is generally believed in the art that NK cells are particularly effective against intracellular infections. Intracellular infections are those wherein a portion of the infecting pathogen resides within cells of the subject.

For example, intracellular infections can be caused by one or more bacteria selected from: *Ehrlichia* (e.g., obligate, intracellular bacteria that can appear as small cytoplasmic inclusions in lymphocytes and neutrophils such as *Ehrlichia sennetsu, Ehrlichia canis, Ehrlichia chaffeensis, Ehrlichia phagocytophilia,* or the like); *Listeria* (e.g., *Listeria monocytogenes*); *Legionella* (e.g., *Legionella pneumophila*); *Rickettsiae* (e.g., *Rickettsiae prowazekii, Rickettsiae typhi, Rickettsiae mooseri, Rickettsiae rickettsii, Rickettsiae tsutsugamushi, Rickettsiae sibirica; Rickettsiae australis; Rickettsiae conorii; Rickettsiae akari; Rickettsiae burnetii*); *Chlamydia* (e.g., *Chlamydia psittaci; Chlamydia pneumoniae; Chlamydia trachomatis,* or the like); *Mycobacterium* (*Mycobacterium tuberculosis; Mycobacterium marinum; Mycobacterium Avium* Complex; *Mycobacterium bovis; Mycobacterium scrofulaceum; Mycobacterium ulcerans; Mycobacterium leprae* (Leprosy, Hansen's Bacillus)); *Brucella* (e.g., *Brucella melitensis; Brucella abortus; Brucella suis; Brucella canis*); genus *Coxiella* (e.g., *Coxiella burnetii*); or the like. Thus, in some embodiments, the subject can have an intracellular bacterial infection caused by a bacterium selected from the genera *Ehrlichia; Listeria; Legionella; Rickettsiae; Chlamydia; Mycobacterium; Brucella;* and *Coxiella.*

In various embodiments, the subject having an NK cell-responsive disorder can be in need of treatment for a bacterial infection from one or more upper respiratory tract bacteria. Examples of upper respiratory tract bacteria include those belonging genera such as *Legionella, Pseudomonas,* and the like. In some embodiments, the bacteria can be *Pseudomonas aeruginosa*. In particular embodiments, the bacteria can be *Legionella pneumophila* (e.g., including serogroups 1, 2, 3, 4, 5, 6, 7, 8, and the like), *Legionella dumoffli, Legionella longbeacheae, Legionella micdadei, Legionella oakridgensis, Legionella feelei, Legionella anisa, Legionella sainthelensi, Legionella bozemanii, Legionella gormanii, Legionella wadsworthii, Legionella jordanis,* or *Legionella gormanii.*

In some embodiments, the subject having an NK cell-responsive disorder can be in need of treatment for a bacterial infection from one that causes acute bacterial exacerbation of chronic bronchitis (ABECB) in the subject. Typically, ABECB can be caused by *Streptococcus pneumoniae, Haemophilus influenzae, Haemophilus parainfluenzae,* or *Moraxella catarrhalis.*

In some embodiments, the subject having an NK cell-responsive disorder can be in need of treatment for a bacterial infection from one that causes acute community acquired pneumonia (CAP) in the subject. Typically, CAP can be caused by *Streptococcus pneumoniae, Haemophilus influenzae, Moraxella catarrhalis, Mycoplasma pneumoniae, Chlamydia pneumoniae,* or *Klebsiella pneumoniae*. In a particular embodiment, the CAP can be caused by drug resistant bacteria, e.g., a multi-drug resistant strain of *Streptococcus pneumoniae.*

In various embodiments, the subject having an NK cell-responsive disorder can be in need of treatment for a bacterial infection from *Streptococcus pneumoniae, Haemophilus influenzae, Haemophilus parainfluenzae, Moraxella catarrhalis, Mycoplasma pneumoniae, Chlamydia pneumoniae, Klebsiella pneumoniae, Staphylococcus aureus, Streptococcus pyogenes, Acinetobacter lwoffi, Klebsiella oxytoca, Legionella pneumophila,* or *Proteus vulgaris.*

In various embodiments, the subject having an NK cell-responsive disorder can be in need of treatment for a bacterial infection from maxillary sinus pathogenic bacteria. As used herein, maxillary sinus pathogenic bacteria is a bacterial strain isolated from acute or chronic maxillary sinusitis, or, for example, a maxillary sinus isolate of *Staphylococcus aureus, Streptococcus pneumoniae, Haemophilus* spp., *Moraxella catarrhalis,* an anaerobic strain of non-fermentative Gram negative bacilli, *Neisseria meningitides* or β-haemolytic *Streptococcus*. In various embodiments, maxillary sinus pathogenic bacteria can include a bacterial strain isolated from acute or chronic maxillary sinusitis; a maxillary sinus isolate of *Staphylococcus aureus, Streptococcus pneumoniae, Haemophilus* spp., *Moraxella catarrhalis,* an anaerobic strain of non-fermentative Gram negative bacilli,

*Neisseria meningitidis*, β-haemolytic *Streptococcus*, *Haemophilus influenzae*, an Enterobacteriaceae, a non-fermentative Gram negative bacilli, *Streptococcus pneumoniae*, *Streptococcus pyogenes*, a methicillin-resistant *Staphylococcus* spp., *Legionella pneumophila*, *Mycoplasma* spp. and *Chlamydia* spp., *Haemophilus influenzae*, *Haemophilus parainfluenzae*, *Peptostreptococcus*, *Bacteroides* spp., and *Bacteroides urealyticus*.

In various embodiments, the subject having an NK cell-responsive disorder can be in need of treatment for a bacterial infection that causes a urinary tract infection (UTI) in the subject. Examples of UTIs include urethritis, cystitis, prostatitis, pyelonephritis (acute, chronic, and xanthogranulomatous), and hematogenous UTI (e.g., from bacteremia with virulent bacilli such as *Salmonella*, *Staphylococcus aureus*, and the like). Typically, UTIs can be caused by gram-negative aerobic bacteria, e.g., *Escherichia* (e.g., *Escherichia coli*), *Klebsiella*, *Proteus*, *Enterobacter*, *Pseudomonas*, and *Serratia*; gram-negative anaerobic bacteria; gram-positive bacteria, e.g., Enterococci (e.g., *Enterococcus faecalis*) and *Staphylococcus* sp (e.g., *Staphylococcus saprophyticus*, *Staphylococcus aureus*, and the like); *Mycobacterium tuberculosis*; and sexually transmitted bacterial infections (e.g., *Chlamydia trachomatis*, *Neisseria gonorrhoeae*, and the like).

In certain embodiments, the subject having an NK cell-responsive disorder can be in need of treatment for infections from microorganisms that cause sexually transmitted diseases, for example, *Treponema pallidum*; *Trichomonas vaginalis*; *Candidia* (*Candida albicans*); *Neisseria gonorrhoeae*; *Chlamydia trachomatis*; *Mycoplasma genitalium*, *Ureaplasma urealyticum*; *Haemophilus ducreyi*; *Calymmatobacterium granulomatis* (formerly *Donovania granulomatis*); herpes simplex viruses (HSV-1 or HSV-2); human papillomavirus [HPV]; human immunodeficiency virus (HIV); various bacterial (Shigella, *Campylobacter*, or *Salmonella*), viral (hepatitis A), or parasitic (Giardia or amoeba, e.g., *Entamoeba dispar* (previously *Entamoeba histolytica*); or the like.

Thus, in various embodiments, the subject having an NK cell-responsive disorder can be in need of treatment for an infection resulting in upper respiratory tract bacterial infection, acute bacterial exacerbation of chronic bronchitis; acute community acquired pneumonia, maxillary sinus pathogenic bacteria; a urinary tract infection; or a sexually transmitted infection.

It is believed that the methods can be particularly effective for treating a subject with a viral infection. Thus, in various embodiments, a subject having an NK cell-responsive disorder can be in need of treatment for infection from viruses such as Picornaviruses (e.g., Polio Virus, rhinoviruses and certain echoviruses and coxsackieviruses); Parvoviridae (Human Parvovirus B19); Hepatitis, e.g, Hepadnavirus (Hepatitis B); Papovavirus (JC Virus); Adenovirus (Human Adenovirus); Herpesvirus (e.g., Cytomegalovirus, Epstein Barr Virus (Mononucleosis), Mononucleosis-Like Syndrome, Roseola Infantum, Varicella Zoster Virus (Chicken Pox), Herpes Zoster (Shingles), Herpes Simplex Virus (Oral Herpes, Genital Herpes)), Poxvirus (Smallpox); Calicivirus (Norwalk Virus), Arbovirus (e.g., Togavirus (Rubella virus, Dengue virus), Flavivirus (Yellow Fever virus), Bunyavirus (California Encephalitis Virus), Reovirus (Rotavirus)); Coronavirus (Coronavirus); Retrovirus (Human Immunodeficiency Virus 1, Human Immunodeficiency Virus 2); Rhabdovirus (Rabies Virus), Filovirus (Marburg Virus, Ebola virus, other hemorrhagic viral diseases); Paramyxovirus (Measles Virus, Mumps Virus); Orthomyxovirus (Influenza Virus); Arenavirus (Lassa Fever); human T-cell Lymphotrophic virus type I and II (HTLV-I, HTLV II); human papillomavirus (HPV); or the like. Thus, in various embodiments, the subject can have an infection caused by a virus selected from Picornavirus; Parvoviridae; Hepatitis virus; Papovavirus; Adenovirus; Herpesvirus, Poxvirus; Calicivirus; Arbovirus; Coronavirus; a Retrovirus; Rhabdovirus; Paramyxovirus; Orthomyxovirus; Arenavirus; human T-cell Lymphotrophic virus; human papillomavirus; and human immunodeficiency virus.

In some embodiments, a subject having an NK cell-responsive disorder can be in need of treatment for an infection from a virus or an infection thereof such as human immunodeficiency virus-1, human immunodeficiency virus-2, Cytomegalovirus, Epstein Barr Virus, Mononucleosis-Like Syndrome, Roseola Infantum, Varicella Zoster Virus, Herpes Zoster, Herpes Simplex Virus, or hepatitis.

It is believed that the methods can be particularly effective for treating a subject with a parasitic infection. Thus, in various embodiments, a subject having an NK cell-responsive disorder can be in need of treatment for an infection from Plasmodia (e.g., Plasmodia falciparum, Plasmodia vivax, Plasmodia ovale, and Plasmodia malariae, typically transmitted by anopheline mosquitoes); *Leishmania* (transmitted by sandflies and caused by obligate intracellular protozoa, e.g., *Leishmania donovani*, *Leishmania infantum*, *Leishmania chagasi*, *Leishmania mexicana*, *Leishmania amazonensis*, *Leishmania venezuelensis*, *Leishmania tropica*; *Leishmania major*; *Leishmania aethiopica*; and the subgenus *Viannia*, *Leishmania Viannia braziliensis*, *Leishmania Viannia guyanensis*, *Leishmania Viannia panamensis*, and *Leishmania Viannia peruviana*); *Trypanosoma* (e.g., sleeping sickness caused by *Trypanosoma brucei gambiense*, and *Trypanosoma brucei rhodesiense*); amoebas of the genera *Naegleria* or *Acanthamoeba*; pathogens such as genus *Entamoeba* (*Entamoeba histolytica* and *Entamoeba dispar*); *Giardia lamblia*; *Cryptosporidium*; *Isospora*; *Cyclospora*; *Microsporidia*; *Ascaris lumbricoides*; infection with blood flukes of the genus *Schistosoma* (e.g.; *S. haematobium*; *S. mansoni*; *S. japonicum*; *S. mekongi*; *S. intercalatum*); Toxoplasmosis (e.g., *Toxoplasma gondii*); *Treponema pallidum*; *Trichomonas vaginalis*; or the like.

In some embodiments, the subject having an NK cell-responsive disorder can have an infection caused by a protozoa selected from *Toxoplasma gondii*, *Trypanosoma brucei gambiense*, *Trypanosoma brucei rhodesiense*, *Leishmania donovani*, *Leishmania infantum*, *Leishmania chagasi*, *Leishmania mexicana*, *Leishmania amazonensis*, *Leishmania venezuelensis*, *Leishmania tropica*; *Leishmania major*; *Leishmania aethiopica*; and the subgenus *Viannia*, *Leishmania Viannia braziliensis*, *Leishmania Viannia guyanensis*, *Leishmania Viannia panamensis*, *Leishmania Viannia peruviana*, *Plasmodia falciparum*, *Plasmodia vivax*, *Plasmodia ovale*, and *Plasmodia malariae*.

In the last century, antibiotics were developed that led to significant reductions in mortality. Unfortunately, widespread use has led to the rise of antibiotic resistant bacteria, e.g., methicillin resistant *Staphyloccocus aureus* (MRSA), vancomycin resistant enterococci (VRE), and penicillin-resistant *Streptococcus pneumoniae* (PRSP). Some bacteria are resistant to a range of antibiotics, e.g., strains of *Mycobacterium tuberculosis* resist isoniazid, rifampin, ethambutol, streptomycin, ethionamide, kanamycin, and rifabutin. In addition to resistance, global travel has spread relatively unknown bacteria from isolated areas to new populations. Furthermore, there is the threat of bacteria as biological weapons. These bacteria may not be easily treated with existing antibiotics.

It is believed that the compounds of the invention can be particularly effective for treating a subject for drug-resistant pathogens, for example, drug resistant bacteria, or pathogens for which no drugs are available, e.g., many viruses. Without wishing to be bound by theory, it is believed that because the compounds of the invention can act by increasing NK cell activity, and thus the NK cells can kill infective microorganisms or infected cells separately from any direct action of the compounds on the pathogen or infected cells. Thus, it is believed that the compounds of the invention can have at least one mode of action that is separate from typical anti-infective drugs such as antibiotics which can typically act directly on the bacteria themselves.

Drug resistant pathogens can be resistant to at least one and typically multiple agents, for example, drug resistant bacteria can be resistant to one antibiotic, or typically at least two antibiotics such as penicillin, Methicillin, second generation cephalosporins (e.g., cefuroxime, and the like), macrolides, tetracyclines, trimethoprim/methoxazole, vancomycin, or the like. For example, in some embodiments, a subject can be treated for bacteria selected from a strain of multiple drug resistant *Streptococcus pneumoniae* (MDRSP, previously known as penicillin resistant *Streptococcus pneumoniae*, PRSP), vancomycin resistant *Enterococcus*, methicillin resistant *Staphylococcus Aureus*, penicillin resistant Pneumococcus, antibiotic resistant *Salmonella*, resistant and multi-resistant *Neisseria Gonorrhea* (e.g., resistant to one, two or more of tetracycline, penicillin, fluoroquinolones, cephalosporins, ceftriaxone (Rocephin), Cefixime (Suprax), Azithromycin, or the like), and resistant and multi-resistant Tuberculosis (e.g., resistant to one, two or more of Isoniazid, Rifampin, Ethambutol, Pyrazinamide, Aminoglycoside, Capreomycin, Ciprofloxacin, Ofloxacin, gemifloxacin, Cycloserine, Ethionamide, para-aminosalicylic acid or the like).

In some embodiments, NK cell activity can be increased in subjects that have an immunodeficiency. In various embodiments, this can be due to decreased or deficient NK cell activity. In some embodiments, the immunodeficiency can be any known immunodeficiency, even those that do not directly impact NK cells. Without wishing to be bound by theory, it is believed that boosting NK cell activity can augment immune function in many immunodeficiency conditions to "make-up" at least in part, for aspects of immunodeficiency separate from those aspects directly concerned with NK cell activity.

In various embodiments, immunodeficiency disorders can include disorders with increased susceptibility to infection, for example, one or more disorders selected from: circulatory and systemic disorders (sickle cell disease, diabetes mellitus, nephrosis, varicose veins, congenital cardiac defects); obstructive disorders (ureteral or urethral stenosis, bronchial asthma, bronchiectasis, allergic rhinitis, blocked Eustachian tubes); integumentary defects (eczema, burns, skull fractures, midline sinus tracts, ciliary abnormalities); primary immunodeficiencies (X-linked agammaglobulinemia, DiGeorge anomaly, chronic granulomatous disease, C3 deficiency); secondary immunodeficiencies (malnutrition, prematurity, lymphoma, splenectomy, uremia, immunosuppressive therapy, protein-losing enteropathy, chronic viral diseases); unusual microbiologic factors (antibiotic overgrowth, chronic infections with resistant organism, continuous reinfection (contaminated water supply, infectious contact, contaminated inhalation therapy equipment)); foreign bodies, trauma (ventricular shunts, central venous catheter, artificial heart valves, urinary catheter, aspirated foreign bodies) allogeneic transplant, graft-versus-host disease, uterine dysfunction (e.g., endometriosis), or the like.

In various embodiments, immunodeficiency disorders can include for example, transient hypogammaglobulinemia of infancy, selective IgA deficiency, X-linked agammaglobulinemian (Bruton's Agammaglobulinemia; Congenital Agammaglobulinemia), common variable immunodeficiency (Acquired Agammaglobulinemia), hyper-IgM immunodeficiency, IgG subclass deficiency, chronic mucocutaneous Candidiasis, combined immunodeficiency, Wiskott-Aldrich syndrome, ataxia-telangiectasia, X-linked lymphoproliferative syndrome, hyper-IgE syndrome (Job-Buckley Syndrome), chronic granulotomatous disease, leukocyte adhesion deficiency (MAC-1/LFA-1/CR3 deficiency), or the like.

In various embodiments, immunodeficiency disorders can include primary immunodeficiency disorders for example: B-cell (antibody) deficiencies (X-linked agammaglobulinemia; Ig deficiency with hyper-IgM (XL); IgA deficiency); IgG subclass deficiencies, Antibody deficiency with normal or elevated Igs, Immunodeficiency with theymoma, Common variable immunodeficiency, Transient hypogammaglobulinemia of infancy); T-cell (cellular) deficiencies (Predominant T-cell deficiency: DiGeorge anomaly, Chronic mucocutaneous candidiasis, Combined immunodeficiency with Igs (Nezelof syndrome), Nucleoside phosphorylase deficiency (AR), Natural killer cell deficiency, Idiopathic CD4 lymphocytopenia, Combined T- and B-cell deficiencies: Severe combined immunodeficiency (AR or XL), Adenosine deaminase deficiency (AR), Reticular dysgenesis, Bare lymphocyte syndrome, Ataxia-telangiectasia (AR), Wiskott-Aldrich syndrome (XL), Short-limbed dwarfism, XL lymphoproliferative syndrome); Phagocytic disorders (Defects of cell movement: Hyperimmunoglobulinemia E syndrome, Leukocyte adhesion defect type 1 (AR), Defects of microbicidal activity: Chronic granulomatous disease (XL or AR), Neutrophil G6PD deficiency, Myeloperoxidase deficiency (AR), Chediak-Higashi syndrome (AR)); Complement disorders (Defects of complement components: Clq deficiency, Defects of control proteins: C1 inhibitor deficiency (D1), Factor I (C3b inactivator) deficiency (ACD), Factor H deficiency (ACD), Factor D deficiency (ACD), Properdin deficiency (XL)); or the like.

In various embodiments, immunodeficiency disorders can include secondary immunodeficiency disorders, for example, one or more conditions selected from: Premature and newborn infants (Physiologic immunodeficiency due to immaturity of immune system); Hereditary and metabolic diseases (Chromosome abnormalities (e.g., Down syndrome), Uremia, Diabetes (i.e., complications from diabetes such as gangrene associated with peripheral circulatory and nerve dysfunction), Malnutrition, Vitamin and mineral deficiencies, Protein-losing enteropathies, Nephrotic syndrome, Myotonic dystrophy, Sickle cell disease); Immunosuppressive agents (Radiation, Immunosuppressive drugs, Corticosteroids, Anti-lymphocyte or anti-thymocyte globulin, Anti-T-cell monoclonal antibodies); Infectious diseases (Congenital rubella, Viral exanthems (e.g., measles, varicella), HIV infection, Cytomegalovirus infection, Infectious mononucleosis, Acute bacterial disease, Severe mycobacterial or fungal disease); Infiltrative and hematologic diseases (Histiocytosis, Sarcoidosis, Hodgkin's disease and lymphoma, Leukemia, Myeloma, Agranulocytosis and aplastic anemia); Surgery and trauma (Burns, Splenectomy, Anesthesia, wounds); and Miscellaneous (SLE, Chronic active hepatitis, Alcoholic cirrhosis, Aging, Anticonvulsive drugs, Graft-vs.-host disease); or the like.

In certain embodiments, the subject having an NK cell-responsive disorder can be in need of treatment for burns or wounds. Typically, such a wound or burn is a severe injury that places a significant burden on the subject's immune defenses. For example, in some embodiments, the subject is treated for a second or third degree burn covering at least about 5%, 10%, 15%, 20%, 25%, 30%, 40%, 50%, 75%, or more of the surface area of the subject's body. Also, in some embodiments, the subject is treated for a wound or wounds, e.g., an open wound of at least about 1 cm$^2$, 2 cm$^2$, 5 cm$^2$, 10 cm$^2$, 20 cm$^2$, 50 cm$^2$ or larger, or 1%, 2%, 3%, 4%, 5%, 10%, 15%, or more of the surface area of the subject's body; or one or more incisions penetrating the skin totaling at least 1 cm, 2 cm, 3 cm, 4 cm, 5 cm, 7 cm, 10 cm, 20 cm, 25 cm, 50 cm in length; an amputation; and the like.

In various embodiments, the subject having an NK cell-responsive disorder can have an infection caused by antibiotic resistant bacteria. In some embodiments, the subject can have an infection caused by a bacterium selected from multiple drug resistant *Streptococcus pneumoniae*, vancomycin resistant *Enterococcus*, methicillin resistant *Staphylococcus aureus*, penicillin resistant Pneumococcus, antibiotic resistant *Salmonella*, resistant/multi-resistant *Neisseria gonorrhea*, and resistant/multi-resistant Tuberculosis. In some embodiments, the subject can have a bacterial infection resistant to at least one antibiotic selected from penicillin, Methicillin, second generation cephalosporins, macrolides, tetracyclines, trimethoprim/methoxazole, vancomycin, tetracycline, fluoroquinolones, ceftriaxone, Cefixime, Azithromycin, Isoniazid, Rifampin, Ethambutol, Pyrazinamide, Aminoglycoside, Capreomycin, Ciprofloxacin, Ofloxacin, gemifloxacin, Cycloserine, Ethionamide, and para-aminosalicylic acid.

Thus, various embodiments, the subject having an NK cell responsive disorder can have an immunodeficiency disorder. In some embodiments, the subject can have a primary immunodeficiency disorder. In some embodiments, the subject can have a secondary immunodeficiency disorder.

In some embodiments, immunodeficiency disorders can include uremia, diabetes (infective complications thereof, malnutrition, vitamin and mineral deficiencies, protein-losing enteropathies, nephrotic syndrome, myotonic dystrophy, sickle cell disease; or the like.

In some embodiments, immunodeficiency disorders can be cause or be partially caused by immunosuppressive agents, e.g., radiation, immunosuppressive drugs, corticosteroids, anti-lymphocyte or anti-thymocyte globulin, anti-T-cell monoclonal antibodies; or the like.

In some embodiments, immunodeficiency disorders can caused or partially caused by surgery and trauma, e.g., burns, splenectomy, anesthesia, wounds, implanted medical devices; or the like.

In some embodiments, immunodeficiency disorders can include chronic fatigue syndrome (chronic fatigue immune dysfunction syndrome); Epstein-Barr virus infection, post viral fatigue syndrome, post-transplantation syndrome (host-graft disease), exposure to nitric oxide synthase inhibitors, aging, severe combined immunodeficiency, variable immunodeficiency syndrome, and the like.

Increasing NK cell activity would also be beneficial for treating subjects with disorders including, but not limited to a neurodegenerative disorder. As used herein, a neurodegenerative disorder involves degradation of neurons such as cereberal, spinal, and peripheral neurons (e.g., at neuromuscular junctions), more typically degradation of cerebral and spinal neurons. Neurodegenerative disorders can include Alzheimers' disease; Huntington's disease; Parkinson's disease; spinal/bulbar muscular atrophy (e.g., Kennedy's disease), spinocerebellar ataxic disorders, and other neuromuscular atrophies; familial amyotrophic lateral sclerosis; ischemia; seizure; hypothermia; hyperthermia; burn trauma; atherosclerosis; radiation exposure; glaucoma; toxin exposure; mechanical injury; inflammation; epileptic seizure, injury-induced seizure, chemically-induced seizure, or other diseases associated with superoxide dismutase (SOD) mutations; and the like. Neurodegenerative disorders can also include degradation of neurons caused by ischemia, seizure, thermal stress, radiation, toxin exposure, infection, injury, and the like. Ischemia can damage tissue through multiple routes, including oxygen depletion, glucose depletion, oxidative stress upon reperfusion, and/or glutamate toxicity, and the like. Ischemia can result from an endogenous condition (e.g., stroke, heart attack, and the like), from accidental mechanical injury, from surgical injury (e.g., reperfusion stress on transplanted organs), and the like. Alternatively, tissues that can be damaged by ischemia include neurons, cardiac muscle, liver tissue, skeletal muscle, kidney tissue, pulmonary tissue, pancreatic tissue, and the like.

Other disorders in which increasing NK cell activity would be beneficial include disorders due to thermal stress, (thermal stress includes hyperthermia (e.g., from fever, heat stroke, burns, and the like) and hypothermia); radiation damage, e.g., due to visible light, ultraviolet light, microwaves, cosmic rays, alpha radiation, beta radiation, gamma radiation, X-rays, and the like, (for example, the damage could be radiation damage to non-cancerous tissue in a subject treated for cancer by radiation therapy); mechanical injury, e.g., trauma from surgery, accidents, certain disease conditions (e.g., pressure damage in glaucoma) and the like; and exposure to a toxin. e.g., exposure to a neurotoxin selected from methamphetamine; antiretroviral HIV therapeutics (e.g., nucleoside reverse transcriptase inhibitors; heavy metals (e.g., mercury, lead, arsenic, cadmium, compounds thereof, and the like), amino acid analogs, chemical oxidants, ethanol, glutamate, metabolic inhibitors, antibiotics, and the like.

Another embodiment of the present invention is a method of treating a subject with a cancer. Optionally, the method of the invention can be used for a multi-drug resistant cancer as described below. The method comprises the step of administering an effective amount of a compound of formula (I) through (XVII) and Table 1, or a pharmaceutically acceptable salt thereof. Preferably, one or more additional anti-cancer drugs are co-administered with a compound of the invention. Examples of anti-cancer drugs are described below. Preferably, the co-administered anti-cancer drug is an agent that stabilizes mictotubules, such as Taxol® or a taxane derivative.

As noted above, one embodiment of the present invention is directed to treating subjects with a cancer. "Treating a subject with a cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as tissue or serum components).

In another embodiment, a compound of the invention can be administered as adjuvant therapy to prevent the reoccurrence of cancer. For example, stage II and stage III melanoma are typically treated with surgery to remove the melanoma followed by chemotherapeutic treatment to prevent the reoccurrence of cancer. In one embodiment, one or more additional anti-cancer drugs are co-administered with a compound of the invention as adjuvant therapy. Examples of anti-cancer drugs are described below. In one embodiment, the co-administered anti-cancer drug is an agent that stabilizes mictotubules, such as Taxol® or a taxane derivative. In another embodiment, the co-administered anti-cancer drug is an immunotherapeutic anticancer agent.

Cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, anal carcinoma, esophageal cancer, gastric cancer, hepatocellular cancer, bladder cancer, endometrial cancer, pancreatic cancer, breast cancer, ovarian cancer, prostate cancer, stomach cancer, atrial myxomas, squamous cell carcinoma, basal cell carcinoma, adenocarcinoma, sweat gland carcinoma, sebaceous gland carcinoma, thyroid and parathyroid neoplasms, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small-cell lung cancer, bladder carcinoma, epithelial carcinoma, glioma, pituitary neoplasms, astrocytoma, medulloblastoma, craniopharyngioma, ependymoma, pinealoma, hemangioblastoma, acoustic neuroma, schwannomas, oligodendroglioma, meningioma, spinal cord tumors, melanoma, neuroblastoma, pheochromocytoma, Types 1-3 endocrine neoplasia, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1 (murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic) cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia. Other examples of leukemias are described in Chapter 60 of THE CHEMOTHERAPY SOURCEBOOK, (Michael C. Perry Ed., Williams & Williams (1992)) and Section 36 of HOLLAND FRIE CANCER MEDICINE, (Bast, et al., Eds., 5th ed., B. C. Decker Inc. (2000)). The entire teachings of the preceding references are incorporated herein by reference.

Additional cancers that can be treated or prevented by the methods of the present invention include, but are not limited to oral cavity and pharynx cancers, including tongue, mouth, pharynx, and other oral cavity cancers; digestive system cancers, including esophagus, small intestine, rectum, anus, anal canal, anorectum, liver and intrahepatic bile duct, gallbladder and other biliary, pancreas and other digestive organs; respiratory system cancers, including larynx and bronchus; bone and joint cancers; soft tissue (including heart) cancers; genital system cancers, including uterine cervix, uterine corpus, ovary, vulva, vagina and other female genitals; testis, penis and other male genitals; urinary system cancers, including kidney and renal pelvis, and ureter and other urinary organs; eye and orbit cancers; leukemia, including acute myeloid leukemia and chronic myeloid leukemia.

In one embodiment, the disclosed method is believed to be particularly effective in treating a subject with non-solid tumors such as multiple myeloma. In another embodiment, the disclosed method is believed to be particularly effective against T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1 (acute) cell line); and lymphoma.

In another embodiment, the disclosed method is believed to be particularly effective in treating a subject with an immunosensitive cancer. Immunosensitive cancers are cancers that respond to treatment with immunotherapy. Immunotherapy is described below in more detail. Cancers that respond to immunotherapy include renal cell carcinoma, melanoma (including superficial spreading melanoma, nodular melanoma, acral lentiginous melanoma, lentigo maligna melanoma which is also called Hutchinson's Freckle), multiple myeloma, myeloma, lymphoma, non-small-cell lung cancer, squamous cell carcinoma, basal cell carcinoma, fibrosarcoma and malignant brain tumors.

In another embodiment, the disclosed method is believed to be particularly effective in treating a subject with melanoma.

In another embodiment, the disclosed method is believed to be particularly effective in treating a subject with renal cell carcinoma.

The disclosed method is particularly effective at treating subjects whose cancer has become "drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

Numerous non-cancer diseases involve excessive or hyperproliferative cell growth, termed hyperplasia. As used herein, the terms "proliferative disorder", "hyperproliferative disorder," and "cell proliferation disorder" are used interchangeably to mean a disease or medical condition involving pathological growth of cells. Such disorders include cancer.

Non-cancerous proliferative disorders include smooth muscle cell proliferation, systemic sclerosis, cirrhosis of the liver, adult respiratory distress syndrome, idiopathic cardiomyopathy, lupus erythematosus, retinopathy, e.g., diabetic retinopathy or other retinopathies, cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, desmoid tumors and the like.

Smooth muscle cell proliferation includes proliferative vascular disorders, for example, intimal smooth muscle cell hyperplasia, restenosis and vascular occlusion, particularly stenosis following biologically- or mechanically-mediated vascular injury, e.g., vascular injury associated with balloon angioplasty or vascular stenosis. Moreover, intimal smooth muscle cell hyperplasia can include hyperplasia in smooth muscle other than the vasculature, e.g., hyperplasia in bile duct blockage, in bronchial airways of the lung in asthma patients, in the kidneys of patients with renal interstitial fibrosis, and the like.

Non-cancerous proliferative disorders also include hyperproliferation of cells in the skin such as psoriasis and its varied clinical forms, Reiter's syndrome, pityriasis rubra pilaris, and hyperproliferative variants of disorders of keratinization (e.g., actinic keratosis, senile keratosis), scleroderma, and the like.

An "effective amount" is the quantity of compound in which a beneficial clinical outcome is achieved when the compound is administered to a subject. For example, when a compound of the invention is administered to a subject with a cancer, a "beneficial clinical outcome" includes a reduction in tumor mass, a reduction in metastasis, a reduction in the severity of the symptoms associated with the cancer and/or an increase in the longevity of the subject compared with the absence of the treatment. When a compound of the invention is administered to a subject with a an Hsp70-responsive disorder or an NK cell-responsive disorder, a "beneficial clinical outcome" includes reduction in the severity or number of symptoms associated with the disorder, elimination of an infection, or increase in the longevity of the subject compared with the absence of the treatment. The precise amount of compound administered to a subject will depend on the type and severity of the disease or condition and on the characteristics of the subject, such as general health, age, sex, body weight and tolerance to drugs. It may also depend on the degree, severity and type of cancer. The skilled artisan will be able to determine appropriate dosages depending on these and other factors. Effective amounts of the disclosed compounds typically range between about 1 mg/m$^2$ per day and about 10 grams/m$^2$ per day, and preferably between 10 mg/m$^2$ per day and about 5 grams/m$^2$. When co-administered with another anti-cancer agent for the treatment of cancer, an "effective amount" of the second anti-cancer agent will depend on the type of drug used. Suitable dosages are known for approved anti-cancer agents and can be adjusted by the skilled artisan according to the condition of the subject, the type of cancer being treated and the compound of the invention being used.

The bis(thio-hydrazide amide) disclosed herein can be prepared by the methods described in U.S. Pat. Nos. 7,385,084, 6,762,204 and 6,800,660, U.S. application Ser. Nos. 11/432,307 (filed 11 May 2006), 11/502,590 (filed Aug. 10, 2006), and 11/157,213 (filed Jun. 20, 2005), and also according to methods described in U.S. Publication No. 2004/0225016. The entire teachings of these patents and applications are incorporated herein by reference.

The present invention is illustrated by the following examples, which are not intended to be limiting in any way.

Example 1

Oral Administration of Compounds of the Invention Using Various Formulations in Nonclinical Species Methods:

The pharmacokinetics of compounds of the invention were compared in mouse, rat and dog by either intravenous or oral administration in various formulations including drug powder in capsules or in combination with generally recognized as safe (GRAS) excipients. After administration in animals, blood samples were collected at the appropriate time points and plasma was obtained for bioanalysis. Compounds were extracted by protein precipitation and analyzed by LC-UV or LC-MS/MS. PK analysis was performed by noncompartmental analysis using WinNonlin. Oral bioavailability (% F) was calculated based on AUC of Compound 1.

Results:

When Compound 1 powder in capsule was dosed, % F of Compound 1 was less than 5% in rats and dogs. In contrast, Compound 19 dramatically improved % F (>80%) in dogs, reaching the exposure observed in humans following intravenous administration. Solution formulations using GRAS excipients also yielded higher % F (up to 70% in all three species).

Preparation of Formulations:

The concentrations of Compound 1 used for the oral formulations is shown in Table 1, below:

TABLE 1

| Formulation | Compound 1 Concentration (mg/mL) |
| --- | --- |
| TPGS/PEG400 | 5 to 10 |
| Nanoparticles | 5 to 10 |
| Phospholipid | 5 to 10 |
| HP-β-CD | 5 to 8 |
| 0.5% MC suspension | 5 to 10 |

Aqueous Formulations:

For the aqueous formulations of Compounds 19 and 26, the salt was dissolved in either 0.9% saline or 5% dextrose at the concentration of 5~10 mg/mL.

Stock Solution of Compound 1 in DMSO:

200 mg of Compound 1 was dissolved in 1 mL of DMSO.

HP-β-CD Formulations:

For HP-β-CD, Compound 1 was first dissolved in DMSO and diluted with HP-β-CD aqueous solution (20% HP-β-CD in water (w/v)) (final concentration of DMSO was 5%), then lyophilized and reconstituted (see the procedure below).

In order to prepare HP-β-CD aqueous solution, 20 g of HP-β-CD was weighed in 100 mL volumetric flask and the volume was adjusted with Milli-Q water (20% w/v). The compound was vortexed and sonicated until the compound was totally dissolved. 95 mL of HP-β-CD aqueous solution was removed. 5 mL of the Compound 1 DMSO stock solution was added while vortexing (5% DMSO (v/v)). The solution was mixed well and sonicated for ~5 min and filtered through 0.2 mm filter before HPLC analysis.

Lyophilization/Reconstitution:

The solution was frozen in acetone/dry ice and stored in −80° C. freezer overnight. The sample was freeze dried for 2 days and reconstituted with saline.

Nanoparticle Formulation:

The nanoparticle formulation was prepared using 5% of Compound 1 and 1.25% of Pluronic F108 Prill Surfactant (polyoxypropylene-polyoxyethylene block copolymer) (w/w). It was diluted with saline or D5W to appropriate concentrations before dosing to animals.

Phospholipid Formulations:

Phospholipid formulations may be prepared according to any method known in the art such as:

A) Preparation of a 10 mL of transfer medium containing 60.0 mg/mL of Compound 1. Weigh 600 mg of micronized Compound 1 in a closed 10 mL volumetric flask. Add 9.0 mL in portions of the placebo transfer medium and vortex until complete dissolution of the drug substance. Adjust to 10.0 mL by adding more the transfer medium and homogenize.

This 60.0 mg/mL solution should be filtered trhoug a 0.22 μM PVDF sterile filter.

B) Instantaneous loading to obtain 100 mL of a 5.0 mg Compound 1/mL lipid dispersion. Prior to starting the instantaneous loading, allow the lipid dispersion and the transfer medium to equilibrate to room temperature.

Instantaneous loading of the lipid dispersion with drug substance is performed by slow (30-60 seconds) injection of 8.33 mL (one volume parts, density=1.04) of the drug loaded medium (60.0 mg Compound 1/mL) into 91.67 mL (eleven part, density=1.00) of lipid dispersion while continuously gently swirling the vial to produce a slightly turbid dispersion.

This 5.0 mg Compound 1/mL lipid dispersion should be filtered through a 0.22 μM PVDF sterile filter.

In-Life Study

Compounds 1, 19, and Y in various formulations was dosed orally or intravenously to mice, rats, and dogs as shown in Table 2.

TABLE 2

List of PK studies

| Species | Gender | Test Article | Route of Administration | Formulation | Dose (mg/kg) |
|---|---|---|---|---|---|
| CD-1 mouse | F | Compound 1 | IV Bolus | EES (solution) | 10 |
|  |  | Compound 1 | PO | TPGS/PEG400 (solution) | 100 |
| SD rat | M | Compound 1 | IV Bolus | EES (solution) | 25 |
|  |  | Compound 1 | PO | Capsule (Powder) | 50 |
|  |  | Compound 1 | PO | 0.5% MC (Suspension) | 50 |
|  |  | Compound 1 | PO | Nanoparticles (Colloidal dispersion) | 50 |
|  |  | Compound 1 | PO | TPGS/PEG400 (solution) | 50 |
|  |  | Compound 19 | PO | Capsule (Powder) | 50 |
|  |  | Compound 26 | PO | Capsule (Powder) | 50 |
| SD rat | M | Compound 1 | IV Bolus | Phospholipid | 50 |
|  |  | Compound 1 | PO | Phospholipid | 50 |
|  |  | Compound 1 | IV Bolus | HP-β-CD/saline | 80 |
|  |  | Compound 1 | PO | HP-β-CD/saline | 80 |
|  |  | Compound 1 | IV Bolus | Lyophilized HP-β-CD/saline | 80 |
|  |  | Compound 1 | PO | Lyophilized HP-β-CD/saline | 80 |
| Beagle dog | M | Compound 1 | IV infusion | EES (solution) | 10 |
|  |  | Compound 1 | PO | Capsule (Powder) | 50 |
|  |  | Compound 1 | PO | Nanoparticles (Colloidal dispersion) | 50 |
|  |  | Compound 1 | PO | TPGS/PEG400 (solution) | 50 |
|  |  | Compound 19 | PO | Capsule (Powder) | 50 |
|  |  | Compound 26 | PO | Capsule (Powder) | 50 |

EES: 5% Cremophor EL and 5% ethanol in saline
TPGS: d-α-tocopheryl polyethylene glycol 1000 succinate
PEG 400: polyethylene glycol 400
HP-β-CD/saline: 2-hydroxypropyl-beta-cyclodextrin
MC: methylcellulose Blood was collected into heparinized tubes that contained dithioreitol (DTT; ~2 mg/mL) at each time point. After centrifugation plasma was transferred to a new tube that contained DMSO (Plasma:DMSO ration 2:1 for rat/mouse, 9:1 for dog).

Bioanalysis

The conditions used in the bioanalysis of the compounds of the invention are presented in Table 3.

TABLE 3

Bioanalysis conditions

| Sample preparation | Sample extraction | Protein precipitation (150 μL ACN) |
|---|---|---|
|  | Plasma volume | 50 μL |
|  | Instrument | LC-MS/MS (API365 or API3000) |
| MS condition | MS interface | TIS positive |
|  | Scan | Multiple Reaction Monitoring (MRM) |

TABLE 3-continued

| Bioanalysis conditions | | |
|---|---|---|
| Sample preparation | Sample extraction | Protein precipitation (150 μL ACN) |
| HPLC condition | Column | Waters MS C18, 3.0 × 100 mm, 5 μm |
| | Mobile phase | A: 0.1% formic acid in water<br>B: 0.1% formic acid in acetonitrile |
| | Gradient | Linear (A/B 5/95 → 5/95 in 5 min) |
| | Run time | 9 min |
| | Flow rate | 0.5 mL/min |

PK Analysis

The pharmacokinetic parameters for compounds of the invention were determined from the plasma concentration data using the Noncompartmental Analysis module in WinNonlin, version 5.0 (Pharsight Corporation).

The PK parameters are summarized in Tables 4, 5, and 6. Representative plasma concentration vs time profiles are provided in FIG. 1.

TABLE 4

Mean PK Parameters of Compounds of the Invention

| Species/ Gender | Form | Route | Formulation | Dose[i] (mg/kg) | $t_{1/2}$ (h) | Tmax (h) | Cmax (μg/mL) | $AUC_{inf}$ (μg/mL-h) | % F[ii] |
|---|---|---|---|---|---|---|---|---|---|
| CD-1 Mouse F | Compound 1 | IV Bolus | EES (sol'n) | 10 | 0.9 | 0.083 | 6.50 | 3.95 | — |
| | | PO | TPGS/PEG400 (sol'n) | 100 | 1.0 | 0.25 | 12.4 | 8.64 | 21.9 |
| SD rat M | Compound 1 | IV Bolus | EES (sol'n) | 25 | 1.7 | 0.083 | 29.0 | 9.27 | — |
| | | PO | Capsule (powder) | 50 | NR[iii] | NR[iii] | NR[iii] | NR[iii] | ~0 |
| | | PO | 0.5% MC (suspendsion) | 50 | 3.2 | 0.5 | 0.28 | 1.22 | 6.6 |
| | | PO | Nano-Particles (colloidal dispersion) | 50 | 3.1 | 0.3 | 1.07 | 2.37 | 12.8 |
| | | PO | TPGS/PEG400 (sol'n) | 50 | 2.1 | 0.3 | 1.41 | 2.77 | 14.9 |
| | Compound 19 | PO | Capsule (powder) | 50 | 3.9 | 0.6 | 0.64 | 1.41 | 7.5 |
| | Compound 26 | PO | Capsule (powder) | 50 | 3.7 | 0.9 | 0.25 | 1.08 | 5.7 |
| Beagle Dog M | Compound 1 | 1 h IV Infusion | EES (sol'n) | 10 | 1.2 | 1.0 | 11.6 | 25.8 | — |
| | | PO | Capsule (powder) | 50 | 2.5 | 2.0 | 1.33 | 6.52 | 5.1 |
| | | PO | Nano-Particles (colloidal dispersion) | 50 | 4.8 | 0.8 | 16.8 | 57.5 | 44.6 |
| | Compound 1 | PO | TPGS/PEG400 (sol'n) | 50 | 2.2 | 0.4 | 38.1 | 87.5 | 68.0 |
| | Compound 19 | PO | Capsule (powder) | 50 | 2.1 | 0.8 | 40.4 | 103 | 80.2 |
| | Compound 26 | PO | Capsule (powder) | 50 | 3.0 | 1.0 | 19.7 | 45.6 | 35.4 |

[i]Dosage as Compound 1 (free acid);
[ii]The data for Compound 1 IV bolus (mouse/rat) or infusion (dog) were used as the reference to calculate % F.,
[iii]Not reportable (data did not meet the acceptance criteria).

TABLE 5

Mean PK Parameters of Compound 1

| Species/ Gender | Route | Formulation | Dose (mg/kg) | $t_{1/2}$ (h) | Tmax (h) | Cmax (μg/mL) | $AUC_{inf}$ (μg/mL-h) | % F |
|---|---|---|---|---|---|---|---|---|
| SD Rat M | IV Bolus | Phospholipid | 50 | 0.9 | 0.083 | 95.3 | 29.7 | — |
| | PO | Phospholipid | 50 | 0.9 | 0.25-0.5 | 2.05 | 3.79 | 8.8 |
| | IV Bolus | HP-β-CD/ saline | 80 | 0.8 | 0.083 | 58.8 | 23.7 | — |

TABLE 5-continued

Mean PK Parameters of Compound 1

| Species/Gender | Route | Formulation | Dose (mg/kg) | $t_{1/2}$ (h) | Tmax (h) | Cmax (μg/mL) | $AUC_{inf}$ (μg/mL·h) | % F |
|---|---|---|---|---|---|---|---|---|
| | PO | HP-β-CD/saline | 80 | 1.2 | 0.25-0.5 | 2.21 | 4.33 | 17.5 |
| | IV Bolus | Lyophilized HP-β-CD/saline | 80 | 0.4 | 0.083 | 63.8 | 25.7 | — |
| | PI | Lyophilized HP-β-CD/saline | 80 | 2.3 | 0.25 | 2.55 | 5.19 | 21.3 |

TABLE 6

Mean PK Parameters of Compound 22

| Species/Gender | Route | Formulation | Dose (mg/kg) | $t_{1/2}$ (h) | Tmax (h) | Cmax (μg/mL) | $AUC_{inf}$ (μg/mL·h) | % F |
|---|---|---|---|---|---|---|---|---|
| SD Rat M | IV Bolus | Saline | 25 | 3.7 | 0.083 | 39.1 | 11.62 | — |
| | PO | Saline | 50 | 2.5 | 0.63 | 2.4 | 4.76 | 10.5 |

Summary of Findings:

Overall, Compound 1 was quickly absorbed and reached Cmax in 2 hours, and declined in a mono- or bi-phasic manner. The pharmacokinetics of Compound 1 was similar across species, indicating that absorption site was formulation-independent (i.e. upper GI). Key findings are:

Effect of Excipient: Compound 1 Powder Vs Compound 1 in Gras Excipients (Solution)

In both rat and dog, % F of Compound 1 was low (% F=~0% in rat, 5.1% in dog) when Compound 1 (free acid) powder in capsules was dosed. % F was greatly increased when Compound 1 was dissolved in a TPGS/PEG400 and administered as a solution formulation (% F=14.9% in rat, 68.0% in dog).

Compound 1 Suspension Vs Compound 1 Nanoparticles

In rat, two sets of suspension formulations of Compound 1 were administered; a suspension (in 0.5% methylcellulose aqueous solution) prepared by hand-milling (particle size not controlled) or nanoparticles (colloidal dispersion; particle size<100 nm).

The Cmax and AUC values were higher after administration of the nanoparticles than the suspension. In fact, the PK parameters after administration of the nanoparticles were comparable to those with the suspension formulation.

Effect of Dosage Form: Compound 1 (Free Acid) Vs Compounds X and Y (Salts)

As compared to Compound 1, Compounds 19 and 26 showed a higher % F in both rat and dog (% F=5.7% (Compound 19) and 7.5% (Compound 26) in rat; 35.4% (Compound 19) and 80.2% (Compound 26) in dog). Salt forms (>1000 mg/mL for Compound 26, ~50 mg/mL for (Compound 19) have higher aqueous solubility than Compound 1 (<0.1 mg/mL).

Species Differences:

We observed significant species differences in oral availability between rodent and dog. A possible reason may be that first pass metabolism may impact the bioavailability of Compound 1.

Results:

A series of pharmacokinetic studies for compounds of the invention were conducted in mouse, rat and dog with various formulations. Cmax and total systemic exposure of Compound 1 were higher when Compound 1 was formulated in GRAS excipients that could provide solution formulations as compared to the powder in capsule or suspension formulations. In addition, Cmax and total systemic exposure of Compound 1 was higher after administration of Compounds 19 and 26 as compared to Compound 1. Furthermore, when a colloidal dispersion (nanoparticles) of Compound 1 was dosed, Cmax and total systemic exposure of Compound 1 were equivalent to those with solution formulations.

In conclusion, a high oral bioavailability of Compound 1 was obtained using GRAS excipients, colloidal suspension or the salt forms (Compounds 19 and 26).

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition for oral administration comprising an effective amount of a compound represented by the following Structural Formula:

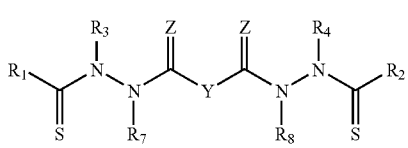

or a pharmaceutically acceptable salt thereof, wherein:
Y is a covalent bond or an optionally substituted straight chained hydrocarbyl group, or, Y, taken together with both >C=Z groups to which it is bonded, is an optionally substituted aromatic group;

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring;

$R_7$-$R_8$ are independently —H, an optionally substituted aliphatic group, or an optionally substituted aryl group; and each Z is independently O or S; and one or more GRAS excipients, wherein the GRAS excipient is TPGS/PEG400.

2. The composition of claim 1, wherein each Z is O, $R_1$ and $R_2$ are the same and $R_3$ and $R_4$ are the same.

3. The composition of claim 2, wherein:

Y is a covalent bond, —C($R_5R_6$)—, trans-(CH=CH)—, cis-(CH=CH)— or —(C≡C)—; and $R_5$ and $R_6$ are each independently —H, an aliphatic or substituted aliphatic group.

4. The composition of claim 3, wherein:

Y is —C($R_5R_6$)—;

$R_1$ and $R_2$ are each an optionally substituted aryl group; and $R_3$ and $R_4$ are each an optionally substituted aliphatic group.

5. The composition of claim 4, wherein $R_5$ is —H and $R_6$ is —H, an aliphatic or substituted aliphatic group.

6. The composition of claim 5, wherein $R_3$ and $R_4$ are each an alkyl group optionally substituted with —OH, halogen, phenyl, benzyl, pyridyl, or $C_1$-$C_8$ alkoxy and $R_6$ is —H or methyl.

7. The composition of claim 6, wherein $R_1$ and $R_2$ are each an optionally substituted phenyl group.

8. The composition of claim 7, wherein the phenyl group represented by $R_1$ and the phenyl group represented by $R_2$ are optionally substituted with one or more groups selected from: —$R^a$, —OH, —Br, —Cl, —I, —F, —O$R^a$, —O—CO$R^a$, —CO$R^a$, —CN, —NCS, —NO$_2$, —COOH, —SO$_3$H, —NH$_2$, —NH$R^a$, —N($R^aR^b$), —COO$R^a$, —CHO, —CONH$_2$, —CONH$R^a$, —CON($R^aR^b$), —NHCO$R^a$, —N$R^c$CO$R^a$, —NHCONH$_2$, —NHCON$R^a$H, —NHCON($R^aR^b$), —N$R^c$CONH$_2$, —N$R^c$CON$R^a$H, —N$R^c$CON($R^aR^b$), —C(=NH)—NH$_2$, —C(=NH)—NH$R^a$, —C(=NH)—N($R^aR^b$), —C(=N$R^c$)—NH$_2$, —C(=N$R^c$)—NH$R^a$, —C(=N$R^c$)—N($R^aR^b$), —NH—C(=NH)—NH$_2$, —NH—C(=NH)—NH$R^a$, —NH—C(=NH)—N($R^aR^b$), —NH—C(=N$R^c$)—NH$_2$, —NH—C(=N$R^c$)—NH$R^a$, —NH—C(=N$R^c$)—N($R^aR^b$), —N$R^d$—C(=NH)—NH$_2$, —N$R^d$—C(=NH)—NH$R^a$, —N$R^d$—C(=NH)—N($R^aR^b$), —N$R^d$—C(=N$R^c$)—NH$_2$, —N$R^d$—C(=N$R^c$)—NH$R^a$, —N$R^d$—C(=N$R^c$)—N($R^aR^b$), —NHNH$_2$, —NHNH$R^a$, —NHN$R^aR^b$, —SO$_2$NH$_2$, —SO$_2$NH$R^a$, —SO$_2$N$R^aR^b$, —CH=CH$R^a$, —CH=C$R^aR^b$, —C$R^c$=C$R^aR^b$, —C$R^c$=CH$R^a$, —C$R^c$=C$R^aR^b$, —CC$R^a$, —SH, —S$R^a$, —S(O)$R^a$, —S(O)$_2R^a$, wherein $R^a$–$R^d$ are each independently an alkyl group, aromatic group, non-aromatic heterocyclic group; or, —N($R^aR^b$), taken together, form an optionally substituted non-aromatic heterocyclic group, wherein the alkyl, aromatic and non-aromatic heterocyclic group represented by $R^a$-$R^d$ and the non-aromatic heterocyclic group represented by —N($R^aR^b$) are each optionally and independently substituted with one or more groups represented by $R^\#$, wherein $R^\#$ is $R^+$, —O$R^+$, —O(haloalkyl), —S$R^+$, —NO$_2$, —CN, —NCS, —N($R^+$)$_2$, —NHCO$_2R^+$, —NHC(O)$R^+$, —NHNHC(O)$R^+$, —NHC(O)N($R^+$)$_2$, —NHNHC(O)N($R^+$)$_2$, —NHNHCO$_2R^+$, —C(O)C(O)$R^+$, —C(O)CH$_2$C(O)$R^+$, —CO$_2R^+$, —C(O)$R^+$, —C(O)N($R^+$)$_2$, —OC(O)$R^+$, —OC(O)N($R^+$)$_2$, —S(O)$_2R^+$, —SO$_2$N($R^+$)$_2$, —S(O)$R^+$, —NHSO$_2$N($R^+$)$_2$, —NHSO$_2R^+$, —C(=S)N($R^+$)$_2$, or —C(=NH)—N($R^+$)$_2$; wherein $R^+$ is —H, a C1-C4 alkyl group, a monocyclic heteroaryl group, a non-aromatic heterocyclic group or a phenyl group optionally substituted with alkyl, haloalkyl, alkoxy, haloalkoxy, halo, —CN, —NO$_2$, amine, alkylamine or dialkylamine; or —N($R^+$)$_2$ is a non-aromatic heterocyclic group, provided that non-aromatic heterocyclic groups represented by $R^+$ and —N($R^+$)$_2$ that comprise a secondary ring amine are optionally acylated or alkylated.

9. The composition of claim 8, wherein the phenyl groups represented by $R_1$ and $R_2$ are optionally substituted with $C_1$-$C_4$ alkyl, $C_1$-$C_4$ alkoxy, $C_1$-$C_4$ haloalkyl, $C_1$-$C_4$ haloalkoxy, phenyl, benzyl, pyridyl, —OH, —NH$_2$, —F, —Cl, —Br, —I, —NO$_2$ or —CN.

10. The composition of claim 9, wherein the phenyl groups represented by $R_1$ and $R_2$ are optionally substituted with —OH, —CN, halogen, $C_1$-$C_4$ alkyl or $C_1$-$C_4$ alkoxy and $R_3$ and $R_4$ are each methyl or ethyl optionally substituted with —OH, halogen or $C_1$-$C_4$ alkoxy.

11. The composition of claim 3, wherein:

Y is —C$R_5R_6$—;

$R_1$ and $R_2$ are both an optionally substituted aliphatic group;

$R_5$ is —H; and $R_6$ is —H or an optionally substituted aliphatic group.

12. The composition of claim 11, wherein $R_1$ and $R_2$ are both a $C_3$-$C_8$ cycloalkyl group optionally substituted with at least one alkyl group.

13. The composition of claim 12, wherein $R_3$ and $R_4$ are both an alkyl group optionally substituted with —OH, halogen, phenyl, benzyl, pyridyl, or $C_1$-$C_8$ alkoxy; and $R_6$ is —H or methyl.

14. The composition of claim 13, wherein $R_1$ and $R_2$ are both cyclopropyl or 1-methylcyclopropyl.

15. The composition of claim 1, wherein the compound is represented by the following Structural Formula:

or a pharmaceutically acceptable salt thereof; wherein:

$R_7$-$R_8$ are both —H, and:

$R_1$ and $R_2$ are both phenyl, $R_3$ and $R_4$ are both methyl, and $R_5$ and $R_6$ are both —H;

$R_1$ and $R_2$ are both phenyl, $R_3$ and $R_4$ are both ethyl, and $R_5$ and $R_6$ are both —H;

$R_1$ and $R_2$ are both 4-cyanophenyl, $R_3$ and $R_4$ are both methyl, $R_5$ is methyl, and $R_6$ is —H;

$R_1$ and $R_2$ are both 4-methoxyphenyl, $R_3$ and $R_4$ are both methyl, and $R_5$ and $R_6$ are both —H;

$R_1$ and $R_2$ are both phenyl, $R_3$ and $R_4$ are both methyl, $R_5$ is methyl, and $R_6$ is —H;

$R_1$ and $R_2$ are both phenyl, $R_3$ and $R_4$ are both ethyl, $R_5$ is methyl, and $R_6$ is —H;

$R_1$ and $R_2$ are both 4-cyanophenyl, $R_3$ and $R_4$ are both methyl, and $R_5$ and $R_6$ are both —H;

$R_1$ and $R_2$ are both 2,5-dimethoxyphenyl, $R_3$ and $R_4$ are both methyl, and $R_5$ and $R_6$ are both —H;

$R_1$ and $R_2$ are both 2,5-dimethoxyphenyl, $R_3$ and $R_4$ are both methyl, $R_5$ is methyl, and $R_6$ is —H;

R₁ and R₂ are both 3-cyanophenyl, R₃ and R₄ are both methyl, and R₅ and R₆ are both —H;
R₁ and R₂ are both 3-fluorophenyl, R₃ and R₄ are both methyl, and R₅ and R₆ are both —H;
R₁ and R₂ are both 4-chlorophenyl, R₃ and R₄ are both methyl, R₅ is methyl, and R₆ is —H;
R₁ and R₂ are both 2-methoxyphenyl, R₃ and R₄ are both methyl, and R₅ and R₆ are both —H;
R₁ and R₂ are both 3-methoxyphenyl, R₃ and R₄ are both methyl, and R₅ and R₆ are both —H;
R₁ and R₂ are both 2,3-dimethoxyphenyl, R₃ and R₄ are both methyl, and R₅ and R₆ are both —H;
R₁ and R₂ are both 2,3-dimethoxyphenyl, R₃ and R₄ are both methyl, R₅ is methyl, and R₆ is —H;
R₁ and R₂ are both 2,5-difluorophenyl, R₃ and R₄ are both methyl, and R₅ and R₆ are both —H;
R₁ and R₂ are both 2,5-difluorophenyl, R₃ and R₄ are both methyl, R₅ is methyl, and R₆ is —H;
R₁ and R₂ are both 2,5-dichlorophenyl, R₃ and R₄ are both methyl, and R₅ and R₆ are both —H;
R₁ and R₂ are both 2,5-dimethylphenyl, R₃ and R₄ are both methyl, and R₅ and R₆ are both —H;
R₁ and R₂ are both cyclopropyl, R₃ and R₄ are both methyl, and R₅ and R₆ are both —H;
R₁ and R₂ are both cyclopropyl, R₃ and R₄ are both ethyl, and R₅ and R₆ are both —H;
R₁ and R₂ are both cyclopropyl, R₃ and R₄ are both methyl, R₅ is methyl, and R₆ is —H;
R₁ and R₂ are both 1-methylcyclopropyl, R₃ and R₄ are both methyl, and R₅ and R₆ are both —H;
R₁ and R₂ are both 1-methylcyclopropyl, R₃ and R₄ are both methyl, R₅ is methyl and R₆ is —H;
R₁ and R₂ are both 1-methylcyclopropyl, R₃ and R₄ are both methyl, R₅ is ethyl, and R₆ is —H;
R₁ and R₂ are both 1-methylcyclopropyl, R₃ and R₄ are both methyl, R₅ is n-propyl, and R₆ is —H;
R₁ and R₂ are both 1-methylcyclopropyl, R₃ and R₄ are both methyl, and R₅ and R₆ are both methyl;
R₁ and R₂ are both 1-methylcyclopropyl, R₃ and R₄ are both ethyl, and R₅ and R₆ are both —H;
R₁ and R₂ are both 1-methylcyclopropyl, R₃ is methyl, R₄ is ethyl, and R₅ and R₆ are both —H;
R₁ and R₂ are both 2-methylcyclopropyl, R₃ and R₄ are both methyl, and R₅ and R₆ are both —H;
R₁ and R₂ are both 2-phenylcyclopropyl, R₃ and R₄ are both methyl, and R₅ and R₆ are both —H;
R₁ and R₂ are both 1-phenylcyclopropyl, R₃ and R₄ are both methyl, and R₅ and R₆ are both —H;
R₁ and R₂ are both cyclobutyl, R₃ and R₄ are both methyl, and R₅ and R₆ are both —H;
R₁ and R₂ are both cyclopentyl, R₃ and R₄ are both methyl, and R₅ and R₆ are both —H;
R₁ and R₂ are both cyclohexyl, R₃ and R₄ are both methyl, and R₅ and R₆ are both —H;
R₁ and R₂ are both cyclohexyl, R₃ and R₄ are both phenyl, and R₅ and R₆ are both —H;
R₁ and R₂ are both methyl, R₃ and R₄ are both methyl, and R₅ and R₆ are both —H;
R₁ and R₂ are both methyl, R₃ and R₄ are both t-butyl, and R₅ and R₆ are both —H;
R₁ and R₂ are both methyl, R₃ and R₄ are both phenyl, and R₅ and R₆ are both —H;
R₁ and R₂ are both t-butyl, R₃ and R₄ are both methyl, and R₅ and R₆ are both —H;
R₁ and R₂ are ethyl, R₃ and R₄ are both methyl, and R₅ and R₆ are both —H; or R₁ and R₂ are both n-propyl, R₃ and R₄ are both methyl, and R₅ and R₆ are both —H.

16. The composition of claim 1, wherein the compound is represented by the following Structural Formula:

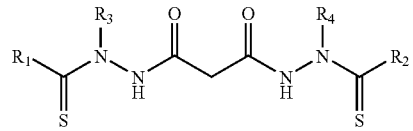

or a pharmaceutically acceptable salt thereof.

17. The composition of claim 16 comprising an effective amount of a compound represented by one of the following Structural Formulas:

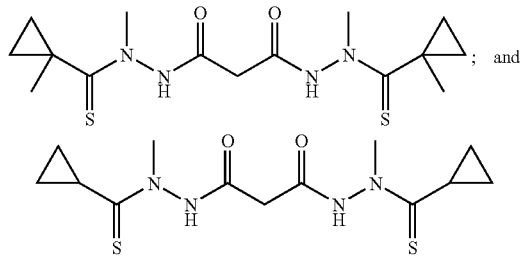

or a pharmaceutically acceptable salt thereof.

18. The composition of claim 16 comprising an effective amount of a compound represented by the following Structural Formula:

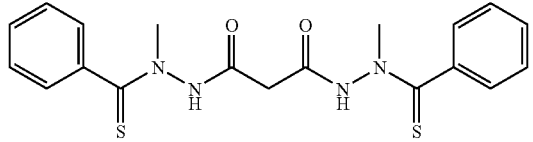 [SMILES: CN(NC(=O)CC(=O)NN(C)C(=S)c1ccccc1)C(=S)c1ccccc1]

or a pharmaceutically acceptable salt thereof.

19. A composition for oral administration comprising an effective amount of a compound represented by the following structural formula:

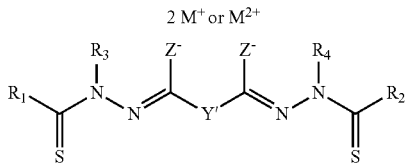

wherein:
Y' is a covalent bond or a substituted or unsubstituted straight chained hydrocarbyl group;
R₁-R₄ are independently —H, an aliphatic group, a substituted aliphatic group, an aryl group or a substituted aryl group, or R₁ and R₃ taken together with the carbon and nitrogen atoms to which they are bonded, and/or R₂ and R₄ taken together with the carbon and nitrogen atoms to which they are bonded, form a non-aromatic heterocyclic ring optionally fused to an aromatic ring;

each Z is independently O or S; and

M⁺ and M²⁺ are independently a pharmaceutically acceptable cations;

and one or more GRAS excipients, wherein the GRAS excipient is TPGS/PEG400.

20. The composition of claim 19, wherein the pharmaceutically acceptable cation is Na⁺ or K⁺.

21. The composition of claim 20, wherein the pharmaceutically acceptable cation is Na⁺.

22. The composition of claim 21 comprising an effective amount of a compound represented by the following structural formula:

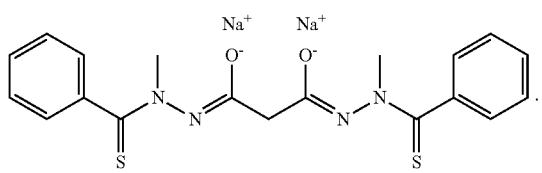 [SMILES: [Na+] ; [Na+] ; CN(/N=C(\[O-])C/C([O-])=N/N(C)C(=S)c1ccccc1)C(=S)c1ccccc1]

23. The composition of claim 21 for oral administration comprising an effective amount of a compound represented by a structural formula selected from:

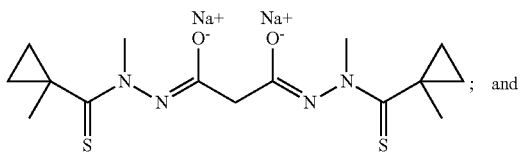; and

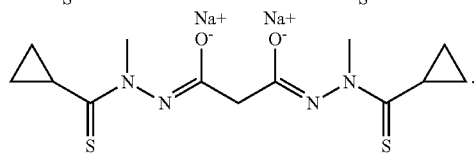.

24. The composition of claim 1 or claim 19, wherein the TPGS/PEG400 is 20% TPGS/80% PEG 400.

25. The composition of claim 1 or claim 19, wherein the composition is present in the form of a capsule.

* * * * *